(12) United States Patent
Raksi

(10) Patent No.: US 8,852,177 B2
(45) Date of Patent: Oct. 7, 2014

(54) SPATIO-TEMPORAL BEAM MODULATOR FOR SURGICAL LASER SYSTEMS

(75) Inventor: Ferenc Raksi, Mission Viejo, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 281 days.

(21) Appl. No.: 13/416,123

(22) Filed: Mar. 9, 2012

(65) Prior Publication Data

US 2013/0237971 A1    Sep. 12, 2013

(51) Int. Cl.
*A61B 18/20*    (2006.01)
*A61F 9/008*    (2006.01)

(52) U.S. Cl.
CPC .............. *A61F 9/008* (2013.01); *A61F 9/0084* (2013.01)
USPC .......................................................... 606/6

(58) Field of Classification Search
CPC ................... A61F 9/0084; A61F 2009/00872; A61F 9/008
See application file for complete search history.

(56) References Cited

U.S. PATENT DOCUMENTS

| | | | |
|---|---|---|---|
| 4,538,608 A | 9/1985 | L'Esperance, Jr. | |
| 4,635,299 A | 1/1987 | MacGovern | |
| 5,541,951 A | 7/1996 | Juhasz et al. | |
| 5,548,234 A | 8/1996 | Turi et al. | |
| 5,549,632 A | 8/1996 | Lai | |
| 5,561,678 A | 10/1996 | Juhasz et al. | |
| 5,656,186 A | 8/1997 | Mourou et al. | |
| 5,789,734 A | 8/1998 | Torigoe et al. | |
| 6,011,640 A * | 1/2000 | Hutton | 359/234 |
| 6,081,543 A | 6/2000 | Liu et al. | |
| 6,099,522 A | 8/2000 | Knopp et al. | |
| 6,203,539 B1 | 3/2001 | Shimmick et al. | |
| 6,220,707 B1 | 4/2001 | Bille | |
| 6,324,191 B1 | 11/2001 | Horvath | |
| 6,610,050 B2 | 8/2003 | Bille | |
| 6,610,051 B2 | 8/2003 | Bille | |
| 6,693,927 B1 | 2/2004 | Horvath et al. | |
| 6,726,680 B1 | 4/2004 | Knopp et al. | |

(Continued)

FOREIGN PATENT DOCUMENTS

| | | |
|---|---|---|
| DE | 10307741 | 9/2004 |
| DE | 10 2005 013949 | 9/2006 |

(Continued)

OTHER PUBLICATIONS

Duma et al., "Determination of Significant Parameters for Eye Injury Risk from Projectiles", Oct. 2005; Journal of Trauma Injury, Infection, and Critical Care, 59(4):960-4, 5 pages.

Gwon et al., "Focal laser photophacoablation of normal and cataractous lenses in rabbits: Preliminary report," May 1995, J. Cataract Refract Surg, 21:282-286, 5 pages.

Jenkins, Francis A., White, Harvey E., Fundamentals of Optics, 4th Ed., 2001, p. 190-191.

(Continued)

*Primary Examiner* — Gary Jackson
*Assistant Examiner* — Scott T. Luan

(57) ABSTRACT

A surgical laser system can include a laser engine to generate a laser beam of laser pulses; a scanning delivery system to direct the laser beam to a target region and to scan the laser beam along a scan-pattern in the target region; and a spatio-temporal modulator to perform a space- and time dependent modulation of the laser beam. The spatio-temporal modulation of the phases or amplitudes of the beam components can reduce or even eliminate uncut regions in the target region, caused by the destructive interference of the beam components brought about by a wrinkling of a portion of the target or by other beam distorting factors.

24 Claims, 17 Drawing Sheets

(56) References Cited

U.S. PATENT DOCUMENTS

| | | | |
|---|---|---|---|
| 6,746,121 B2 | 6/2004 | Ross et al. | |
| 6,751,033 B2 | 6/2004 | Goldstein et al. | |
| 6,908,196 B2 | 6/2005 | Herekar et al. | |
| 6,992,765 B2 | 1/2006 | Horvath et al. | |
| 7,027,233 B2 | 4/2006 | Goldstein et al. | |
| 7,131,968 B2 | 11/2006 | Bendett et al. | |
| 7,145,661 B2 | 12/2006 | Hitzenberger | |
| 7,330,275 B2 | 2/2008 | Raksi | |
| 7,336,366 B2 | 2/2008 | Choma | |
| 7,390,089 B2 | 6/2008 | Loesel et al. | |
| 7,452,080 B2 | 11/2008 | Wiltberger et al. | |
| 7,452,081 B2 | 11/2008 | Wiltberger et al. | |
| 7,522,642 B2 | 4/2009 | Zadoyan et al. | |
| 7,584,756 B2 | 9/2009 | Zadoyan et al. | |
| 7,597,444 B2 | 10/2009 | Rathjen et al. | |
| 7,599,591 B2 | 10/2009 | Andersen et al. | |
| 7,655,002 B2 | 2/2010 | Myers | |
| 7,918,559 B2 | 4/2011 | Tesar | |
| 8,246,609 B2 | 8/2012 | Zickler et al. | |
| 8,262,646 B2 | 9/2012 | Frey et al. | |
| 2003/0053219 A1 | 3/2003 | Manzi | |
| 2004/0059321 A1 | 3/2004 | Knopp et al. | |
| 2004/0059398 A1* | 3/2004 | Yee et al. | 607/89 |
| 2004/0202351 A1 | 10/2004 | Park et al. | |
| 2004/0243112 A1 | 12/2004 | Bendett et al. | |
| 2004/0254568 A1 | 12/2004 | Rathjen | |
| 2005/0228366 A1 | 10/2005 | Kessler et al. | |
| 2006/0084954 A1 | 4/2006 | Zadoyan et al. | |
| 2006/0100613 A1 | 5/2006 | McArdle et al. | |
| 2006/0195076 A1 | 8/2006 | Blumenkranz et al. | |
| 2007/0073279 A1* | 3/2007 | Rowe et al. | 606/11 |
| 2007/0106285 A1 | 5/2007 | Raksi | |
| 2007/0121069 A1 | 5/2007 | Andersen et al. | |
| 2007/0126985 A1 | 6/2007 | Wiltberger et al. | |
| 2007/0129709 A1 | 6/2007 | Andersen et al. | |
| 2007/0129775 A1 | 6/2007 | Mordaunt et al. | |
| 2007/0173791 A1 | 7/2007 | Raksi | |
| 2007/0173795 A1 | 7/2007 | Frey et al. | |
| 2007/0173796 A1 | 7/2007 | Kessler et al. | |
| 2007/0185475 A1 | 8/2007 | Frey et al. | |
| 2007/0219541 A1 | 9/2007 | Kurtz | |
| 2007/0235543 A1 | 10/2007 | Zadoyan et al. | |
| 2007/0282313 A1 | 12/2007 | Huang et al. | |
| 2008/0015553 A1 | 1/2008 | Zacharias | |
| 2008/0033406 A1 | 2/2008 | Andersen et al. | |
| 2008/0077121 A1 | 3/2008 | Rathjen | |
| 2008/0147052 A1 | 6/2008 | Bendett et al. | |
| 2008/0167642 A1 | 7/2008 | Palanker et al. | |
| 2008/0192783 A1 | 8/2008 | Rathjen et al. | |
| 2008/0228176 A1 | 9/2008 | Triebel et al. | |
| 2008/0231807 A1 | 9/2008 | Lacombe et al. | |
| 2008/0269731 A1 | 10/2008 | Swinger et al. | |
| 2008/0281303 A1 | 11/2008 | Culbertson et al. | |
| 2008/0319428 A1 | 12/2008 | Wiechmann et al. | |
| 2008/0319464 A1 | 12/2008 | Bischoff et al. | |
| 2009/0002835 A1 | 1/2009 | Prior et al. | |
| 2009/0012507 A1 | 1/2009 | Culbertson et al. | |
| 2009/0118718 A1 | 5/2009 | Raksi et al. | |
| 2009/0131921 A1 | 5/2009 | Kurtz et al. | |
| 2009/0149841 A1 | 6/2009 | Kurtz | |
| 2009/0171327 A1 | 7/2009 | Kurtz et al. | |
| 2009/0231704 A1 | 9/2009 | Chen | |
| 2009/0296083 A1 | 12/2009 | Saaski et al. | |
| 2009/0299347 A1 | 12/2009 | Vogler et al. | |
| 2010/0004641 A1 | 1/2010 | Frey et al. | |
| 2010/0042079 A1 | 2/2010 | Frey et al. | |
| 2010/0082017 A1 | 4/2010 | Zickler et al. | |
| 2010/0130966 A1 | 5/2010 | Brownell | |
| 2010/0191226 A1 | 7/2010 | Blumenkranz et al. | |
| 2010/0305553 A1* | 12/2010 | Kittelmann et al. | 606/4 |
| 2011/0028958 A1* | 2/2011 | Raksi et al. | 606/6 |
| 2011/0034911 A1 | 2/2011 | Bischoff et al. | |
| 2011/0184392 A1 | 7/2011 | Culbertson et al. | |
| 2011/0205492 A1 | 8/2011 | Rathjen | |
| 2011/0264081 A1 | 10/2011 | Reich et al. | |
| 2012/0136342 A1* | 5/2012 | Bischoff et al. | 606/5 |

FOREIGN PATENT DOCUMENTS

| | | |
|---|---|---|
| EP | 0326760 | 8/1989 |
| EP | 1279386 | 1/2003 |
| EP | 1584310 | 10/2005 |
| EP | 1837696 | 9/2007 |
| JP | 2007-159740 | 6/2007 |
| WO | 98/56298 | 12/1998 |
| WO | 2007/021022 | 2/2007 |
| WO | 2007/056486 | 5/2007 |
| WO | 2008/055506 | 5/2008 |
| WO | 2009/089504 | 7/2009 |

OTHER PUBLICATIONS

Kruger et al., "Experimental Increase in Accommodative Potential after Neodymium: Yttrium—Aluminum-Garnet Laser," Jun. 2001, Ophthalmology 108:2122-2129, 8 pages.

Lindstrom, Cionni, Donnenfeld, and Slade, "The Dawn of Laser Refractive Cataract Surgery" excerpts from Supplement to Cataract & Refractive Surgery Today, Jun. 2011, 6 pages, Sponsored by Alcon Laboratories, Inc., published in the U.S.

PCT International Application No. PCT/US2010/042777, in International Search Report mailed Mar. 25, 2011, 10 pages.

PCT International Application No. PCT/US2010/042786, in International Search Report mailed Apr. 25, 2011, 9 pages.

PCT International Application No. PCT/US2010/042787, in International Search Report mailed Mar. 25, 2011, 11 pages.

PCT International Application No. PCT/US2010/042791, in International Search Report mailed Mar. 25, 2011, 14 pages.

PCT International Application No. PCT/US2010/042796, in International Search Report mailed Mar. 28, 2011, 11 pages.

PCT International Application No. PCT/US2010/042800, in International Search Report mailed Mar. 30, 2011, 9 pages.

PCT International Application No. PCT/US2010/042804, in International Search Report mailed Mar. 30, 2011, 8 pages.

PCT International Application No. PCT/US2010/042957, in International Search Report mailed Apr. 25, 2011, 9 pages.

PCT International Application No. PCT/US2010/042960, in International Search Report mailed Apr. 25, 2011, 9 pages.

PCT International Application No. PCT/US2010/042964, in International Search Report mailed Apr. 25, 2011, 9 pages.

PCT International Application No. PCT/US2010/055968, in International Search Report mailed Jul. 6, 2011, 9 pages.

Ryan et al., "Nd:YAG Laser Photodisruption of the Lens Nucleus Before Phacoemulsification," Oct. 1987, American Journal of Ophthalmology 104:382-386, 5 pages.

Wang, Haifeng and Gan, Fuxi, 2001, "High focal depth with a pure-phase apodizer", Applied Optics, vol. 40, No. 31, 5658-5662, 5 pages.

PCT International Search Report for corresponding International Application No. PCT/US2013/029896, with mailing date Jun. 19, 2013, 3 pages.

An, Lin and Wang, Ruikang K., "Use of a scanner to modulate spatial interferograms for in vivo full-range Fourier-domain optical coherence tomography", Dec. 1, 2007, OPTICS LETTERS, vol. 32(23); pp. 3423-3425.

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27, 7 pages.

European Supplementary European Search Report for EP Application No. 10806836.2 with mailing date Oct. 8, 2012, 4 pages.

Plamann K et al., "Laser parameters, focusing optics, and side effects in femtosecond laser corneal surgery", Proc. of SPIE, vol. 6844 68440W-1-68440W-10, 2008.

* cited by examiner

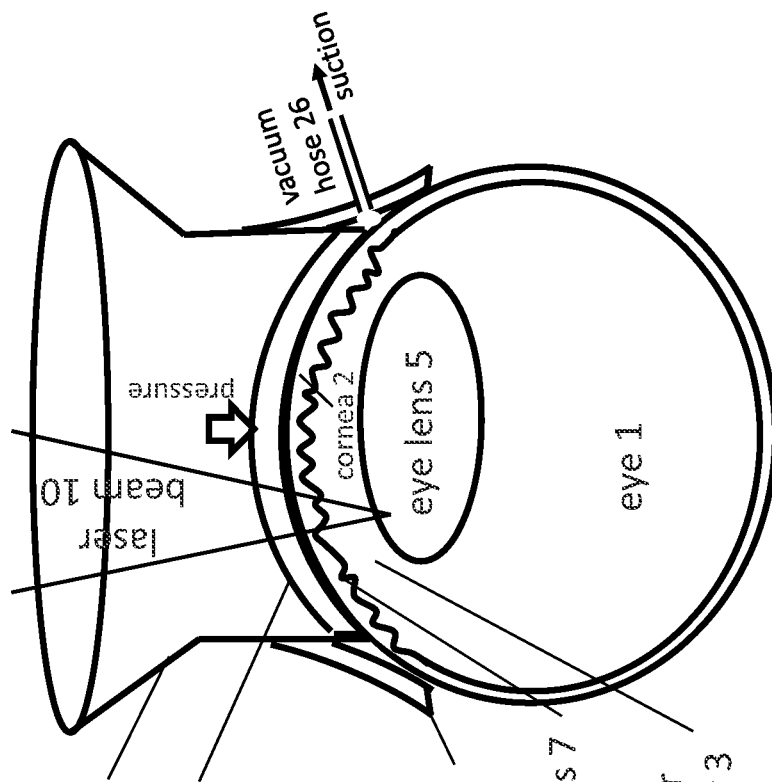
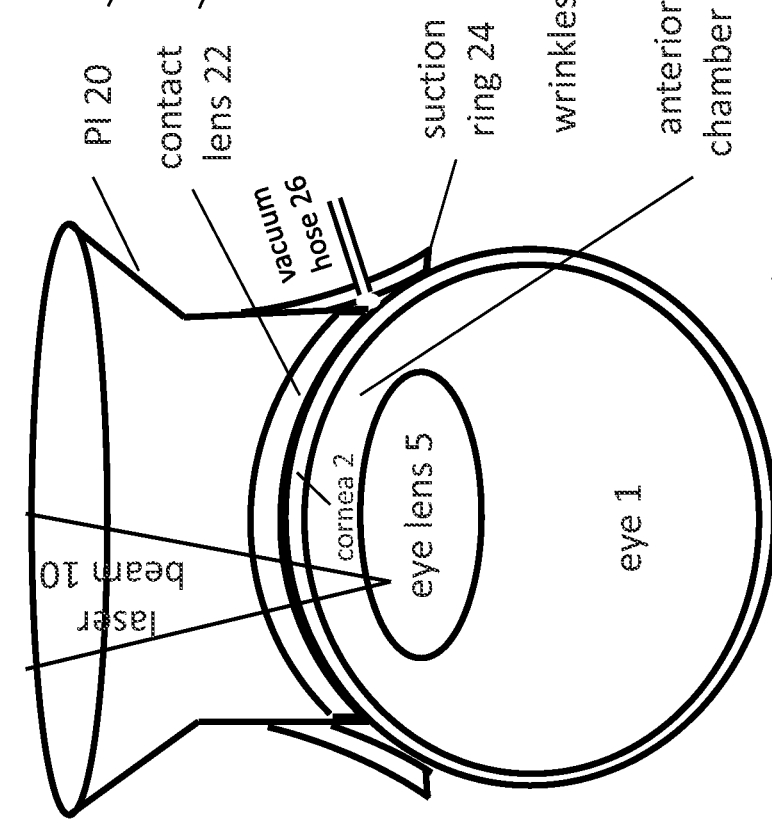
FIG. 1A
FIG. 1B

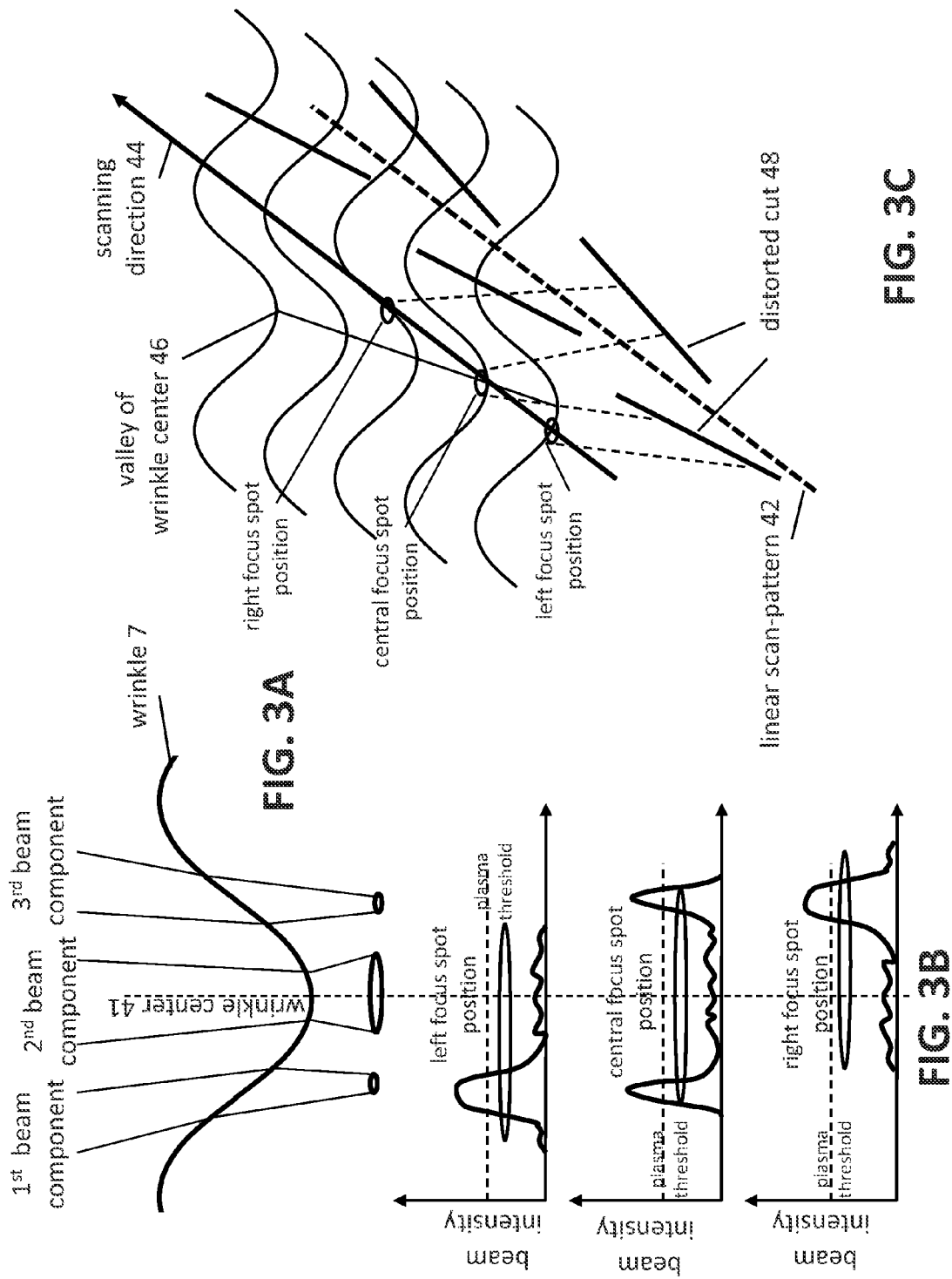

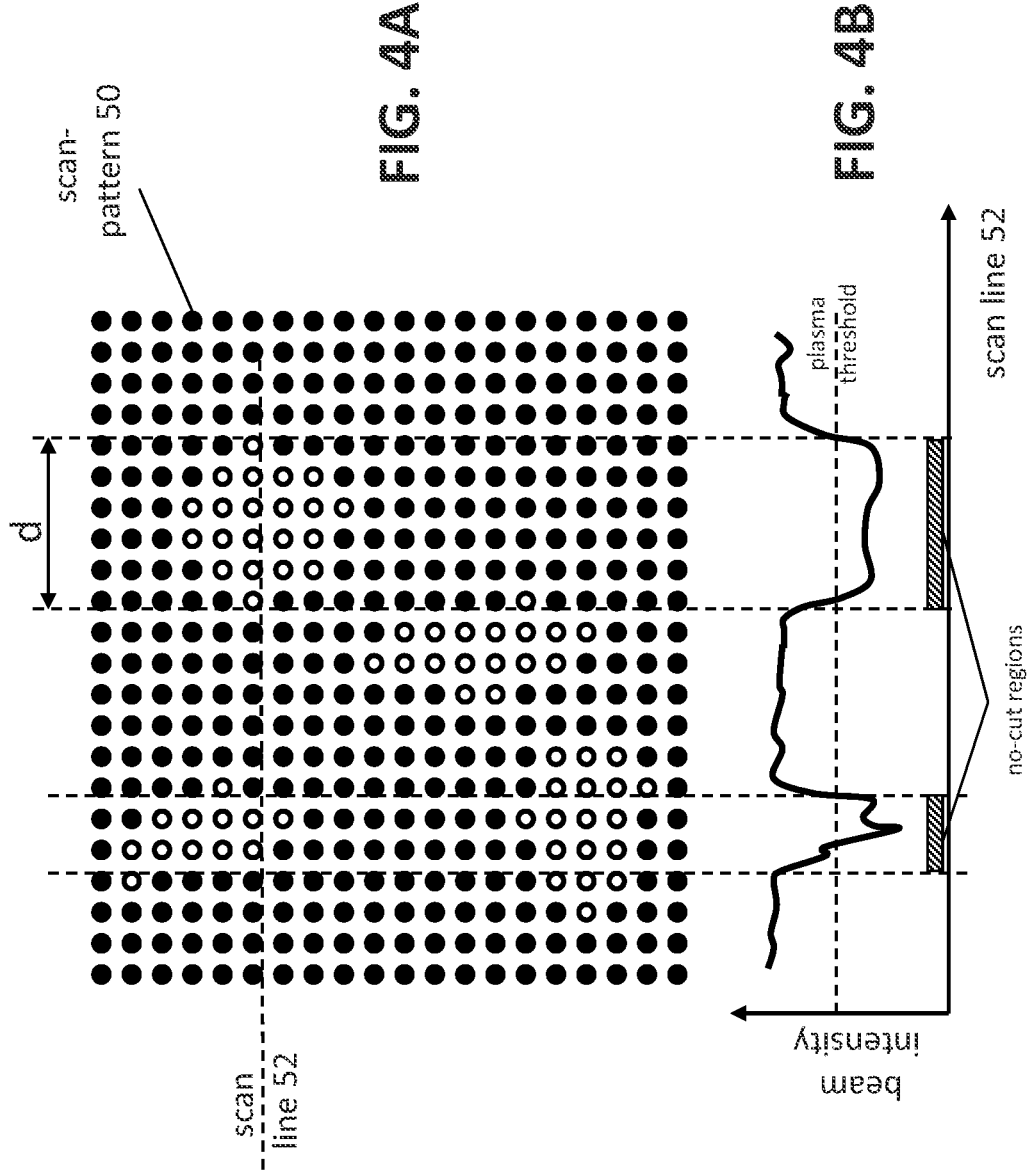

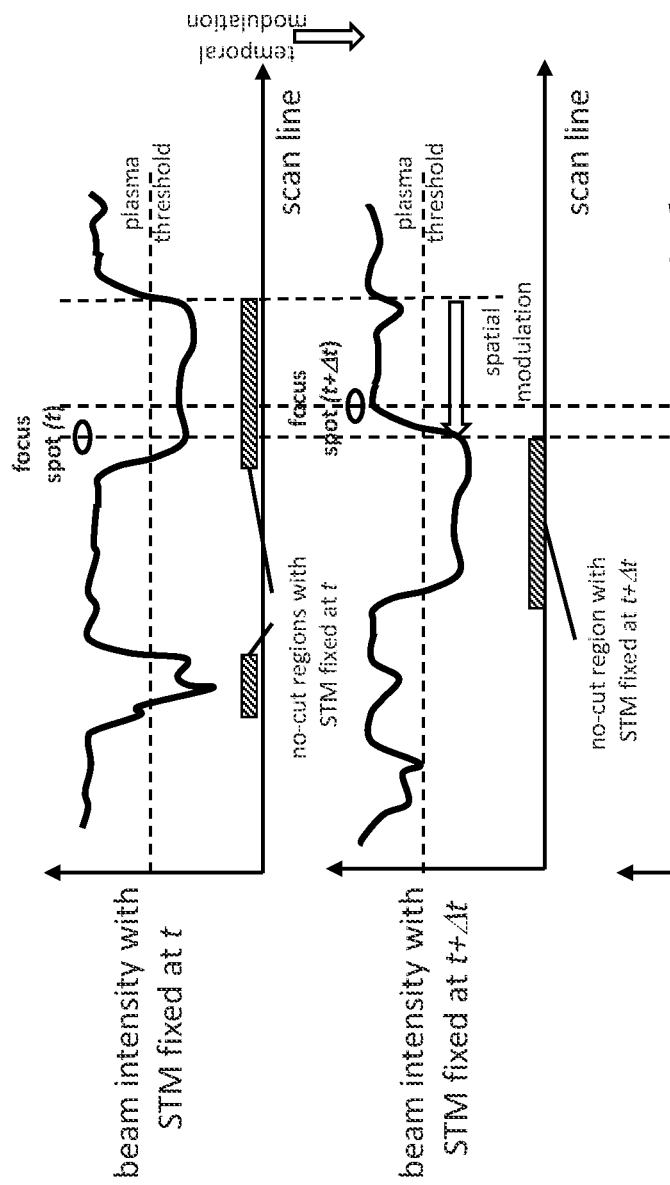

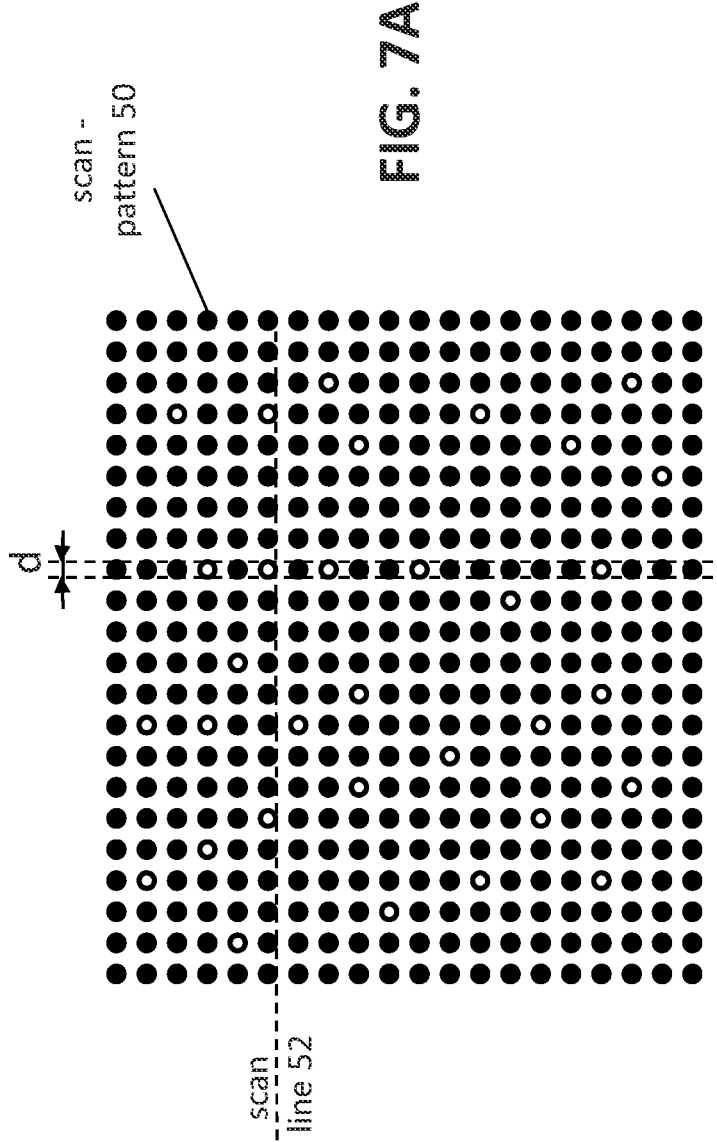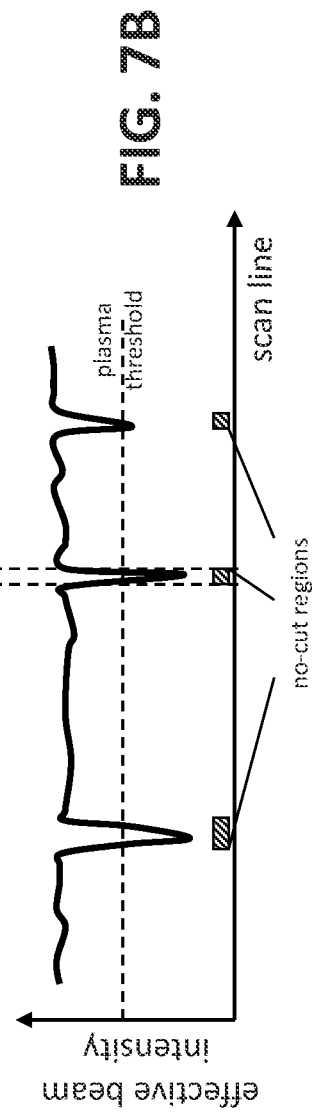

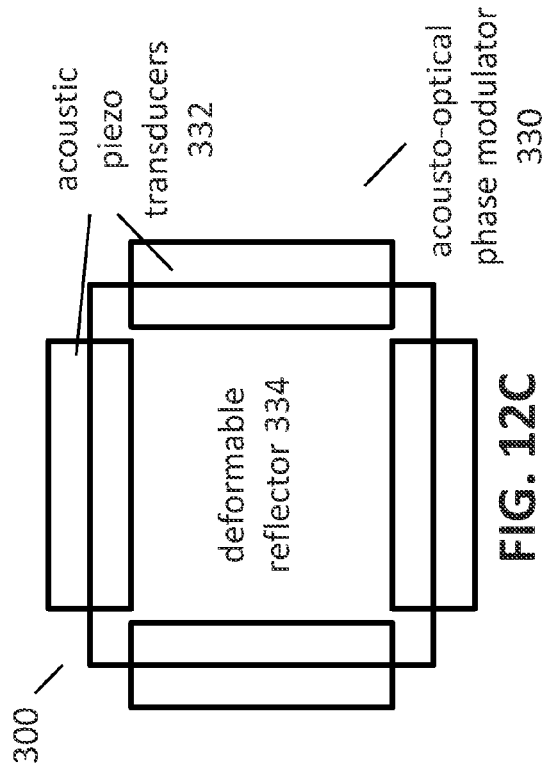
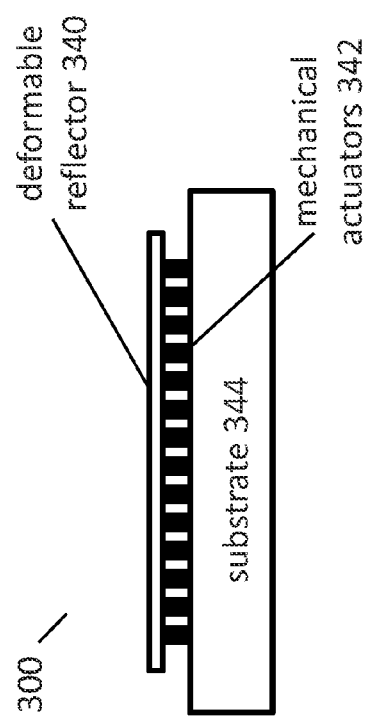
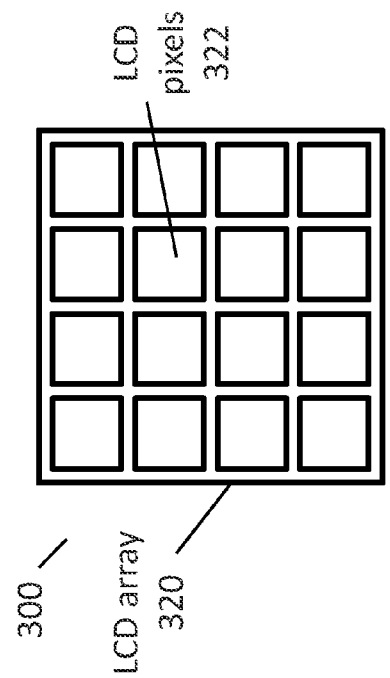
FIG. 12A
FIG. 12B
FIG. 12C
FIG. 12D

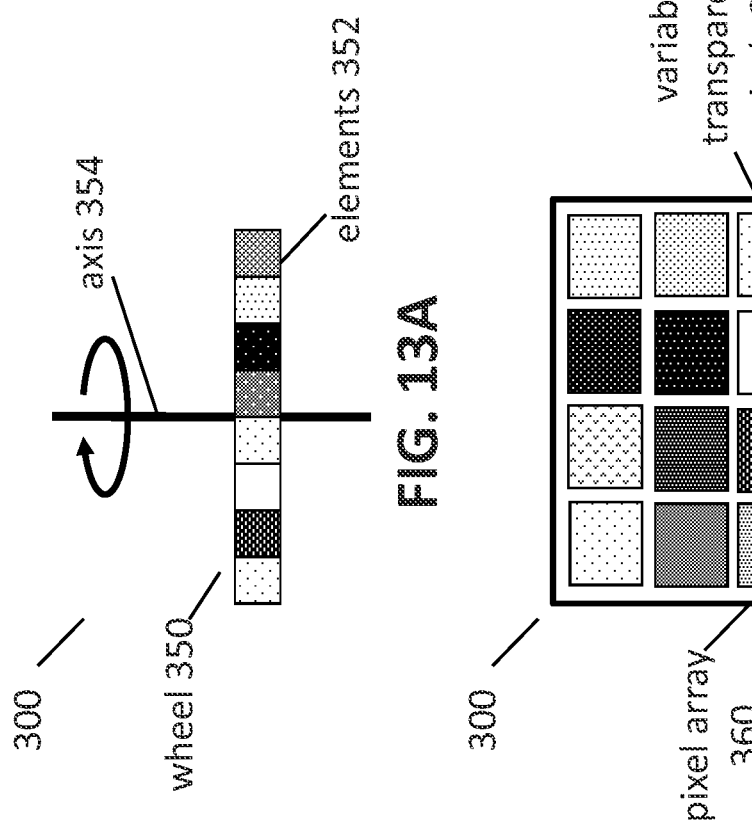

SPATIO-TEMPORAL BEAM MODULATOR FOR SURGICAL LASER SYSTEMS

TECHNICAL FIELD

This patent document relates to surgical laser systems. More precisely, this patent document relates to homogenizing a laser beam by a spatio-temporal beam modulator in ophthalmic surgical laser systems.

BACKGROUND

Surgery with femtosecond ophthalmic lasers is based on generating a pulsed laser beam and delivering the laser pulses by a scanning delivery system through a focusing optics to a sequence of focus spots along a scan-pattern in a target region of an ophthalmic tissue. Each laser pulse can create a plasma or cavitation bubble in the target tissue at the focus spot of the laser beam when the beam intensity or energy density exceeds a plasma or photodisruption threshold. During surgery, the focus spot of the laser beam is scanned along a three dimensional scan-pattern, creating a sequence of these bubbles to form macroscopic surgical cuts or photodisrupted regions.

During the surgery, however, the laser beam can also cause unintended collateral damage away from the focus spot such as excessive heating and shockwaves in the target tissue and light poisoning in the retina. Therefore, surgical systems are designed to deliver the laser beam with an energy density that exceeds the photodisruption threshold, but only marginally to achieve the surgical functionality while minimizing the collateral damage.

The energy density or beam intensity is determined by the energy, duration and repetition rate of the individual laser pulses and the size of the focus spot. Modern surgical laser systems provide high precision and control by using precisely controlled laser sources, refined optical designs, high quality optical parts and an objective with a large numerical aperture to focus the laser beam down to a diffraction limited focus spot with a diameter of a few microns, and do so at all points of the scan-pattern within a surgical volume, or at all scanner positions of the surgical laser system. This high precision makes the modern laser surgical systems capable of maintaining the beam intensity marginally above the plasma threshold along the entire scan-pattern within the surgical volume in ideal or model targets.

Unfortunately, in spite of all the design and manufacturing effort spent on optimizing the laser sources and optics, the focus spot in the ophthalmic target region is often still larger than its diffraction limited value because the target tissue itself often gets distorted, making it different from the ideal or model targets used during the design of the laser optics. Distortions can be also caused by imperfections of the scanning delivery system and the focusing optics. The enlarging of the focus spot caused by any of these distortions can lead to failing surgical performance since it lowers the pulse energy density or beam intensity below the plasma threshold and thus prevents the scanning laser beam from forming the planned surgical cuts, leaving uncut lines or regions in the target region.

This problem of failing surgical performance can become particularly acute during surgical cuts where the targeted tissue is very thin such as a capsulotomy of the thin lens capsular bag during a cataract surgery. Since the targeted tissue is thin, the laser beam scans it only once or only a few times along a loop, as this scan-pattern should be already capable of cutting through the entire thickness of the capsular bag. However, if any one of the above distortions reduces the beam intensity below the plasma threshold along a section of the loop then that section can remain uncut. This uncut section of the capsular bag needs to be cut and separated manually, possibly leading to a tearing of the capsular bag and thus to a substantial lowering of the precision of the cataract surgery. Therefore, there is a need for surgical laser systems that can deliver the laser beam with a pulse energy density that is marginally higher than the plasma threshold in the entire surgical volume even if distortions are present along the beam path either in the target region or in the optical system itself, as such laser systems are capable of cutting the target region according to the scan-pattern in the entire surgical volume without leaving uncut regions or lines.

SUMMARY

An objective of cataract surgery is to direct or deliver a surgical laser beam 10 into an eye 1 through its cornea 2 and anterior chamber 3 to photodisrupt a cataractous target region in a lens 5. FIGS. 1A-D illustrate some of the problems caused by beam distortions in cataract surgery. FIG. 1A illustrates that many surgical laser systems have a patient interface (PI) 20 attached to a distal end of an objective of the laser scanning delivery system. The PI 20 can include a contact lens 22 that makes contact with the cornea 2 to allow a well-controlled entry of the surgical laser beam 10 into the cornea 2. The PI 20 is often outfitted with a suction ring 24 and a vacuum hose 26 for creating a reliable mechanical coupling with the eye 1.

FIG. 1B illustrates that the PI 20 and its contact lens 22 can be coupled to the cornea 2 reliably by applying suction to the vacuum hose 26 that presses the contact lens 22 to the cornea 2. Sometimes, the PI 20 and its contact lens 22 can be additionally pressed against the cornea 2 by its own weight or by a mechanical system such as spring loading.

FIG. 1B also shows that, unfortunately, the pressure caused by the vacuum suction and the mechanical pressure can create wrinkles 7 in the cornea 2, which can cause the above mentioned beam distortions.

FIG. 1C illustrates a mathematical formulation of the distortions or aberrations of the laser beam 10. It is customary to define an aberration as the deviation of a wavefront of the laser beam 10 from a conceptual Gaussian reference sphere segment S of radius R. The Gaussian sphere segment S can be centered on the geometrical focal point $P_0$ of the laser beam 10 and formed by the intersection of the laser beam 10 and an entire Gaussian reference sphere. In many cases, the reference sphere segment S is the pupil of the laser system. The two main classes of distortions or aberrations are phase and amplitude distortions/aberrations. The formulation is presented here for the more typical phase aberrations. Amplitude aberrations can be described in an analogous manner.

It is known from the theory of optical wave propagation that the intensity of light I(P) at a point P in the focal plane that contains the geometrical focus point $P_0$ is given by the absolute value squared of the electromagnetic disturbance, in essence the electric field, with the fast oscillating $e^{i\omega t}$ factor removed:

$$I(P) = |u(P)|^2.$$

According to the Huygens-Fresnel principle, the electric field U(P) at the point P is given by an integral of the beam components E(Q,P) over the Gaussian reference sphere segment S:

$$U(P) = -\frac{i}{\lambda} \int \int_S E(Q, P) dS(Q)$$

$$= -\frac{i}{\lambda} \int \int_S E_0(Q, P) e^{ik\Phi} dS(Q)$$

$$= -\frac{i}{\lambda} \int \int_S A \frac{e^{ik(s-R)} e^{ik\Phi}}{sR} dS(Q)$$

Here, $E(Q,P)$ is the propagating electric field, or beam component that propagates from a $dS(Q)$ vicinity of point Q on the Gaussian reference sphere segment S to the point P of the focal plane near $P_0$, the geometrical focus point. This beam component can be decomposed into $E_0(Q,P)$, the propagating electric field in the absence of a phase aberration and into $e^{ik\Phi}$, representing the phase aberration by a phase aberration function $\Phi$. The undistorted field can be represented as:

$$E_0(Q, P) = A \frac{e^{ik(s-R)}}{Rs}.$$

Here, A is the amplitude of the beam component at point Q, reduced during the propagation to point P by $1/s$, where s is the length of the QP ray from the point Q to point P. Further, $e^{ik(s-R)}$ represents the propagating wave phase factor, acquired by the propagating electromagnetic wave $E_0(Q,P)$ in the absence of aberrations. Finally, $k=2\pi/\lambda$ is the wavenumber and $\lambda$ is the wavelength of the laser beam 10. Discussing the aberration-free beam, for $P=P_0$ $s=R$ and thus the phase factors of the beam components that propagate from the different Q points of the reference sphere segment S to the geometrical focus point $P_0$ add up with maximum constructive interference. Further, as known, the interference remains constructive in a small but finite vicinity of the geometrical focus point $P_0$, broadening the geometrical focus point $P_0$ into a diffraction limited focus spot 32.

FIG. 1D illustrates the beam intensity along a typical scan line in the target region when the laser beam is scanned over an unwrinkled cornea. Since the aberration function is essentially zero in this region, the propagating wave phase factors $e^{ik(s-R)}$ of the beam components $E(Q,P)$ in the Huygens-Fresnel integral can add smoothly and constructively when reaching P points in the vicinity the geometrical focus point $P_0$, thus producing a laser beam 10 with a beam intensity that can remain above the plasma threshold along the shown and the other scan lines within the surgical volume. Therefore, as the laser beam 10 is scanned across the scan lines of the scan-pattern, it can create the intended surgical cuts in the entire surgical volume.

FIG. 1E illustrates that, in contrast to the unwrinkled case of FIG. 1D, if the vacuum suction or the mechanical pressure creates corneal wrinkles 7, then these wrinkles 7 can distort the laser beam 10 by refracting the propagating electric fields, or beam components, to distorted directions, so that their aberration function $\Phi$ in the Huygens-Fresnel integral become different from zero. The corresponding phase factors $e^{ik\Phi}$ can lead to a substantially destructive interference between the beam components, possibly substantially reducing the beam intensity. The magnitude of the corneal phase aberration can be estimated as the product of the amplitude of the wrinkles and the change of the refractive index at the cornea-aqueous humor interface. The refractive index of the cornea is approximately 1.377 while the index of the aqueous humor is 1.337, separated by a difference of 0.04. As an example, for a laser wavelength of 1 micrometer, wrinkles with amplitude of 25 micrometers give approximately $2\pi$ phase aberration. Therefore, in general, for $\Phi>\pi/4$ the phase aberrations can already substantially reduce the beam intensity, and for $\Phi>\pi/2$ the aberrations even reverse the sign of the contributions of the beam components $E(Q,P)$ to the Huygens-Fresnel integral. These destructive interferences can reduce the beam intensity at the focus spot 32 to a value below the plasma threshold and thus preventing the laser beam 10 from photodisrupting the target region and from executing the surgical cuts along the surgical scan-pattern, instead leaving uncut regions behind. In some cases, the single focus spot may even break up into multiple foci, as shown later.

FIGS. 2A-B illustrate a related effect of corneal wrinkling FIG. 2A illustrates that in the absence of corneal wrinkling the focus spot 32 of the laser beam 10 can have a near diffraction limited size of a few microns for a laser beam 10 with wavelength in the 500-1,500 nm range. The scanning delivery system and optics can be designed to deliver the laser beam 10 with an intensity to this focus spot 32 that marginally exceeds the plasma or photodisruption threshold everywhere in the surgical volume and thus is capable of executing the surgical cuts without leaving uncut regions behind.

FIG. 2B illustrates that when the vacuum suction or pressure of the PI 20 creates wrinkles 7 in the cornea 2, then the wrinkles 7 can redirect and refract some beam components to go through the plane of the focus spot 32, or focal plane, of the unwrinkled case smeared over an enlarged aberration focus spot 32. The increase of the focus spot area decreases the beam intensity, possibly below the plasma threshold. Besides causing destructive interference of the phase factors of the beam components, this focus-spot-smearing is an additional mechanism by which corneal wrinkling can reduce the beam intensity below the plasma threshold.

FIGS. 3A-C illustrate one more negative effect of corneal wrinkling FIG. 3A illustrates the previously discussed redirection of beam components in more detail. Three beam components are tracked explicitly. Visibly, the $1^{st}$, $2^{nd}$ and $3^{rd}$ beam components are redirected and refracted differently by the wrinkle 7. The $1^{st}$ and $3^{rd}$ beam components fall on the two sides of the wrinkle 7 that are relatively straight. Therefore, while the $1^{st}$ or $3^{rd}$ beam components get redirected, their focus spots do not get enlarged substantially and thus their beam intensity does not get reduced substantially. In contrast, the $2^{nd}$ beam component is propagating through the substantially curved wrinkle center 41 and thus gets refracted into a wider spatial angle, having its beam smeared out to an enlarged focus spot 32 and therefore having its beam intensity substantially reduced.

FIG. 3B illustrates that the location of the focus spot 32 of the entire laser beam 10 relative to the wrinkle center 41 controls which beam components are present in a laser beam 10 delivered to a particular spot.

FIG. 3B, top panel illustrates the focus spot 32 being in a left focus spot position, left of the wrinkle center 41. In this case the laser beam 10 includes only the $1^{st}$ and $2^{nd}$ beam components, resulting in a beam intensity profile that has one peak from the $1^{st}$ beam component with an intensity above the plasma threshold and a broad feature from the $2^{nd}$ beam component, smeared out to such a degree that its beam intensity is reduced below the plasma threshold. Therefore, the overall beam intensity profile exhibits a narrow peak, noticeably shifted to the left from the center of the focus spot 32. Thus, the laser beam 10 in the left focus spot position cuts the target tissue only partially, only at the location of the peak of the $1^{st}$ beam component but not at the location of the smeared $2^{nd}$ beam component. Moreover, the resulting partial cut will even be shifted from its intended location.

FIG. 3B, center panel illustrates that analogously, when the focus spot 32 is in the central focus spot position around the wrinkle center 41, the laser beam 10 includes all three beam components. In this central focus spot position the sides of the wrinkle 7 redirect the $1^{st}$ and $3^{rd}$ beam components to separate side peaks, while the wrinkle center 41 again smears out the $2^{nd}$ beam component, reducing its intensity. This results in the shown two peaks in the beam intensity profile.

FIG. 3B, bottom panel illustrates the case when the focus spot 32 is in the right focus spot position, to the right of the wrinkle center 41. In this case the laser beam includes only the $2^{nd}$ and $3^{rd}$ beam components, resulting in one peak in the beam intensity profile, noticeably shifted to the right from the center of the focus spot 32.

As mentioned above, the laser systems are often designed so that the beam intensity exceeds the plasma threshold only marginally. Therefore, in the above three cases the beam intensity profile may remain above the plasma threshold only at the peaks of the $1^{st}$ and $3^{rd}$ beam components, whereas it may dip below the plasma threshold for the $2^{nd}$ beam component, smeared out by the wrinkle center 41. Correspondingly, in the left focus spot position the laser beam 10 may create a cut shifted to the left from the center of the focus spot 32; in the central focus spot position the laser beam 10 may create two cuts, shifted to the left and to the right from the center, and finally in the right focus spot position the laser beam 10 may create a cut shifted to the right from the center of the focus spot 32. Further, as mentioned before, these cuts can be only partial cuts, limited to portions of the beam cross section.

FIG. 3C illustrates how a linear scan-pattern 42 can get distorted in the presence of a wrinkled cornea. Such a linear scan-pattern 42 is typical for a capsulotomy over a short segment, eventually looping around in a circle. In a typical case the laser beam 10 is scanned along a scanning direction 44 that is not parallel with a valley of the wrinkle center 46. When the focus spot 32 of the laser beam 10 is scanned left of the wrinkle center 46 through a left focus spot position, the laser beam 10 can create a distorted cut 48 instead of the planned linear scan-pattern 42, shifted to the left from the intended linear scan-pattern 42 as in the top panel of FIG. 3B. When the focus spot 32 is scanned through the central focus spot position, the distorted cut 48 can contain two off-center cuts, shifted to the left and to the right from the single cut of the linear scan-pattern 42, as in the center panel of FIG. 3B. Finally, when the focus spot 32 is scanned through the right focus spot position, the laser beam 10 can create a single cut again, only this time shifted to the right from the linear scan-pattern 42, as in the bottom panel of FIG. 3B.

FIG. 3C illustrates the resulting overall distorted cut 48: instead of the intended linear cut of the linear scan-pattern 42 that would have been created in the absence of the corneal wrinkle 7, a jagged, staggered, partially double-valued cut gets created when the laser beam 10 is scanned across a wrinkled cornea.

FIGS. 4A-B illustrate the analogous problem for a two dimensional (2D) scan-pattern 50. Such a 2D scan-pattern 50 can be used when an ophthalmic layer is to be cut, or a volume is to be photodisrupted. The laser beam 10 can be scanned along the 2D scan-pattern to create a densely packed layer of photodisrupted bubbles. This photodisrupted layer can effectively cut apart the tissue segments on its two sides. However, if the laser beam 10 is distorted by a wrinkled cornea, at several of the intended spots of the scan-pattern 50 the beam intensity may be reduced below the plasma threshold, and thus the laser beam 10 may fail to create the photodisrupted bubbles, as shown in FIG. 4A.

FIG. 4B illustrates that the beam intensity may be reduced below the plasma threshold for extended "no-cut regions" or "uncut regions" of the size d along a typical scan line 52, where d can be comparable to the size of the corneal wrinkles 7. In typical ophthalmic cases, d can vary from about 10 microns to beyond 1 millimeter. Referring back to FIG. 4A, these uncut regions can have a spatial extent beyond a millimeter in one, two or even all three dimensions. Therefore, when the scanning of the laser beam 10 is finished, the intended surgical cuts will be interrupted by extended no-cut regions.

The surgeon may attempt to cut these no-cut regions by re-scanning the entire scan pattern or portions of the scan-pattern 50. However, this is not very effective, since the same wrinkles are still present in the cornea, giving rise to the same aberrations. Thus, the same regions will remain uncut during the second scan. Re-scanning is also time-consuming. Every time the surgeon is forced to repeat a surgical step, valuable surgical time is spent, increasing the probability of undesirable outcomes.

Therefore, the surgeon may be forced to cut the uncut regions manually to complete the surgery, possibly creating jagged edges, leading to the formation of tears in the ophthalmic tissue. These undesirable effects call out for improvements in the surgical laser systems that reduce or eliminate the formation of the uncut regions.

Briefly and generally, embodiments of the invention offer solutions to the above problems by providing a surgical laser system that includes a laser engine, configured to generate a laser beam of laser pulses; a scanning delivery system, configured to direct the laser beam to a target region, and to scan the laser beam along a scan-pattern in the target region; and a spatio-temporal modulator, configured to perform a space- and time dependent modulation of the laser beam.

Other embodiments include a method of homogenizing a laser beam, including: generating a laser beam of laser pulses with a laser engine; directing the laser beam to a target region with a scanning delivery system; scanning the laser beam along a scan-pattern in the target region with the scanning delivery system; and performing a space- and time dependent modulation of the laser beam with a spatio-temporal modulator.

BRIEF DESCRIPTION OF THE DRAWINGS

FIGS. 1A-E illustrate an effect of a wrinkled cornea on an ophthalmic surgical laser beam.

FIGS. 3A-C illustrate an effect of corneal wrinkling on a linear cut.

FIGS. 4A-B illustrate an effect of corneal wrinkling on a two dimensional cut.

FIGS. 6A-C illustrate an effect of a spatio-temporal modulator on a beam intensity in the context of a one dimensional scan-pattern.

FIGS. 7A-B illustrate an effect of a spatio-temporal modulator on a beam intensity in the context of a two dimensional scan-pattern.

FIGS. 12A-D illustrate embodiments of a spatio-temporal modulator.

FIGS. 13A-B illustrate additional embodiments of a spatio-temporal modulator.

DETAILED DESCRIPTION

To address the above described problem of the appearance of extensive no-cut regions caused by the corneal wrinkles distorting the laser beam, this patent document describes embodiments of a surgical laser system that includes a spatio-temporal beam modulator.

Figure 1C:
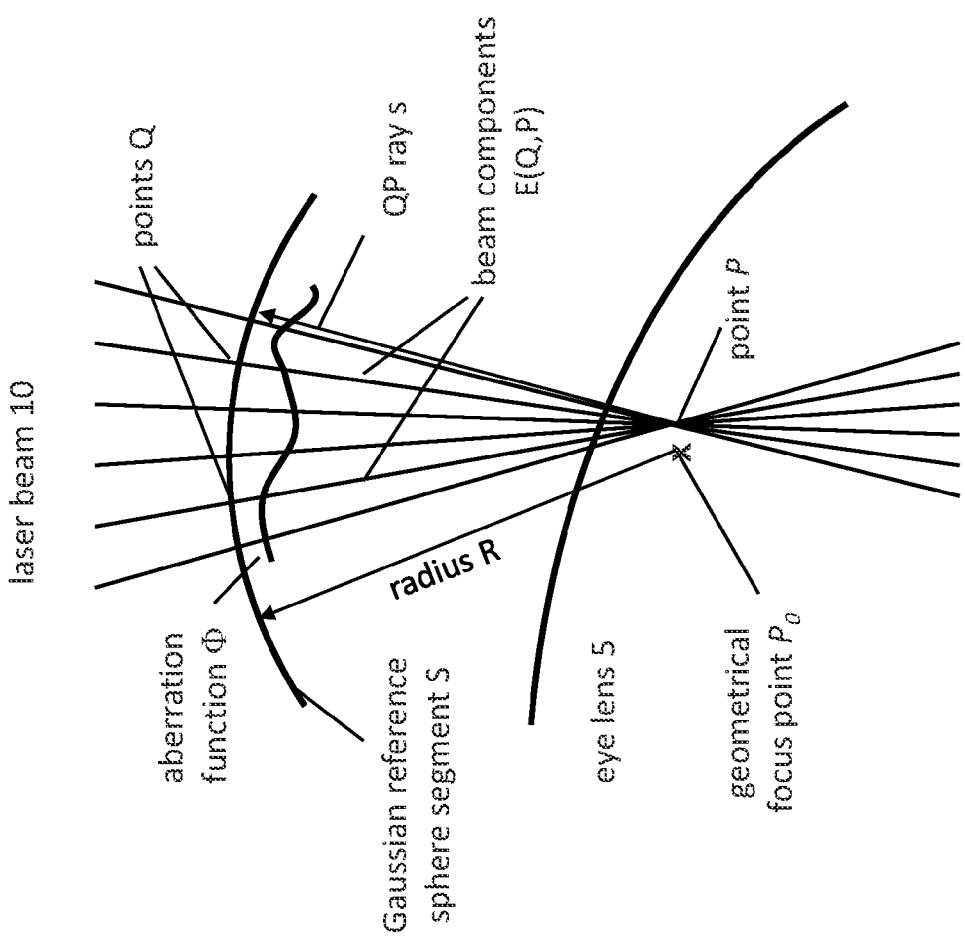
Figure 1E:
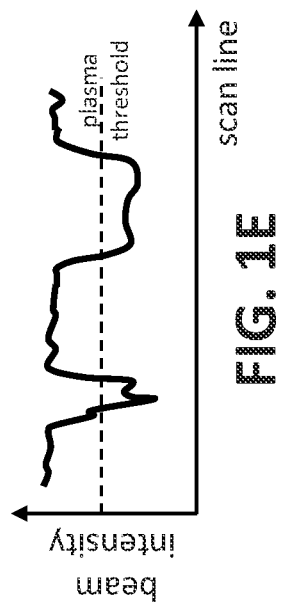
Figure 1D:
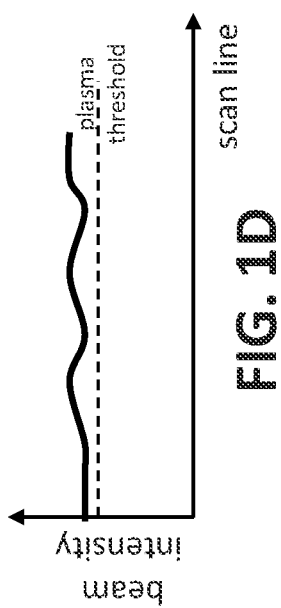
Figure 2A:
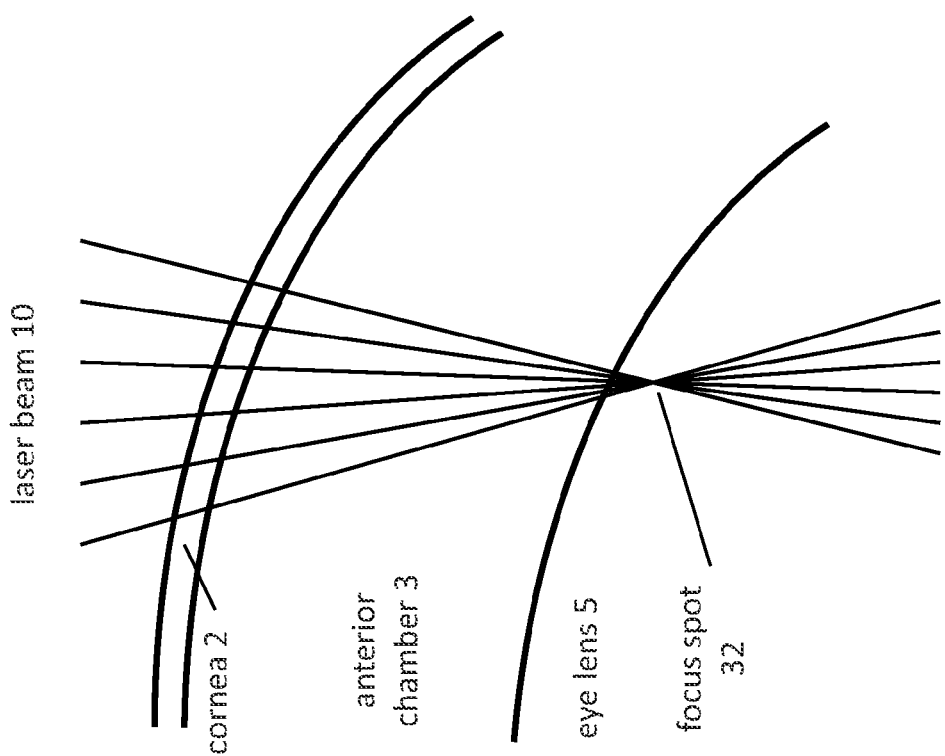
FIGS. 2A-B illustrate an enlargement of a focus spot because of corneal wrinkling.
Figure 2B:
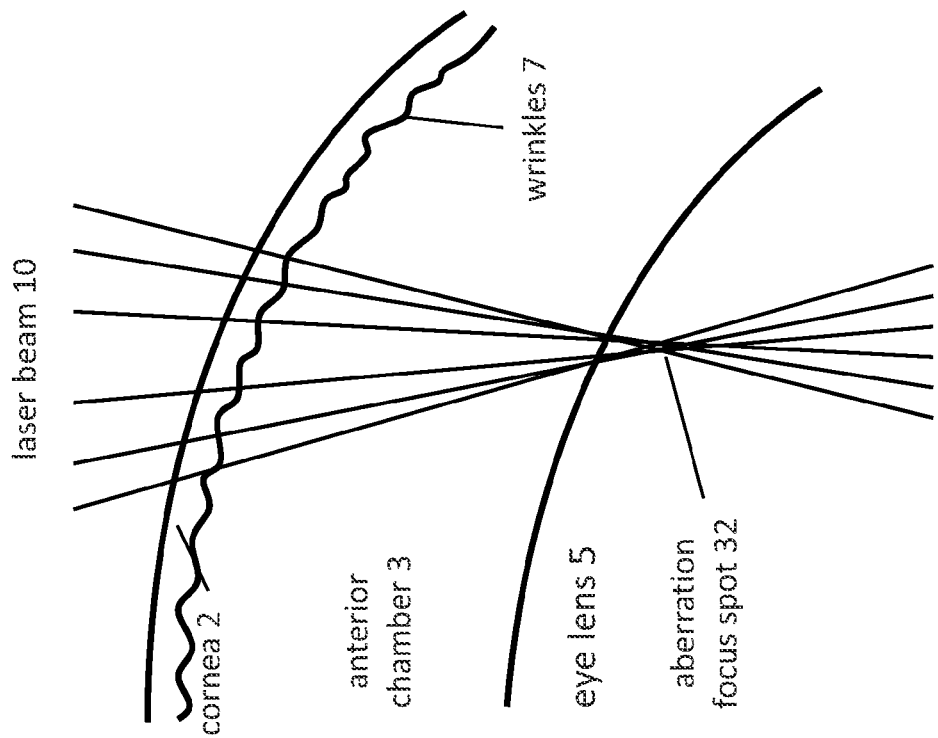
Figure 5:
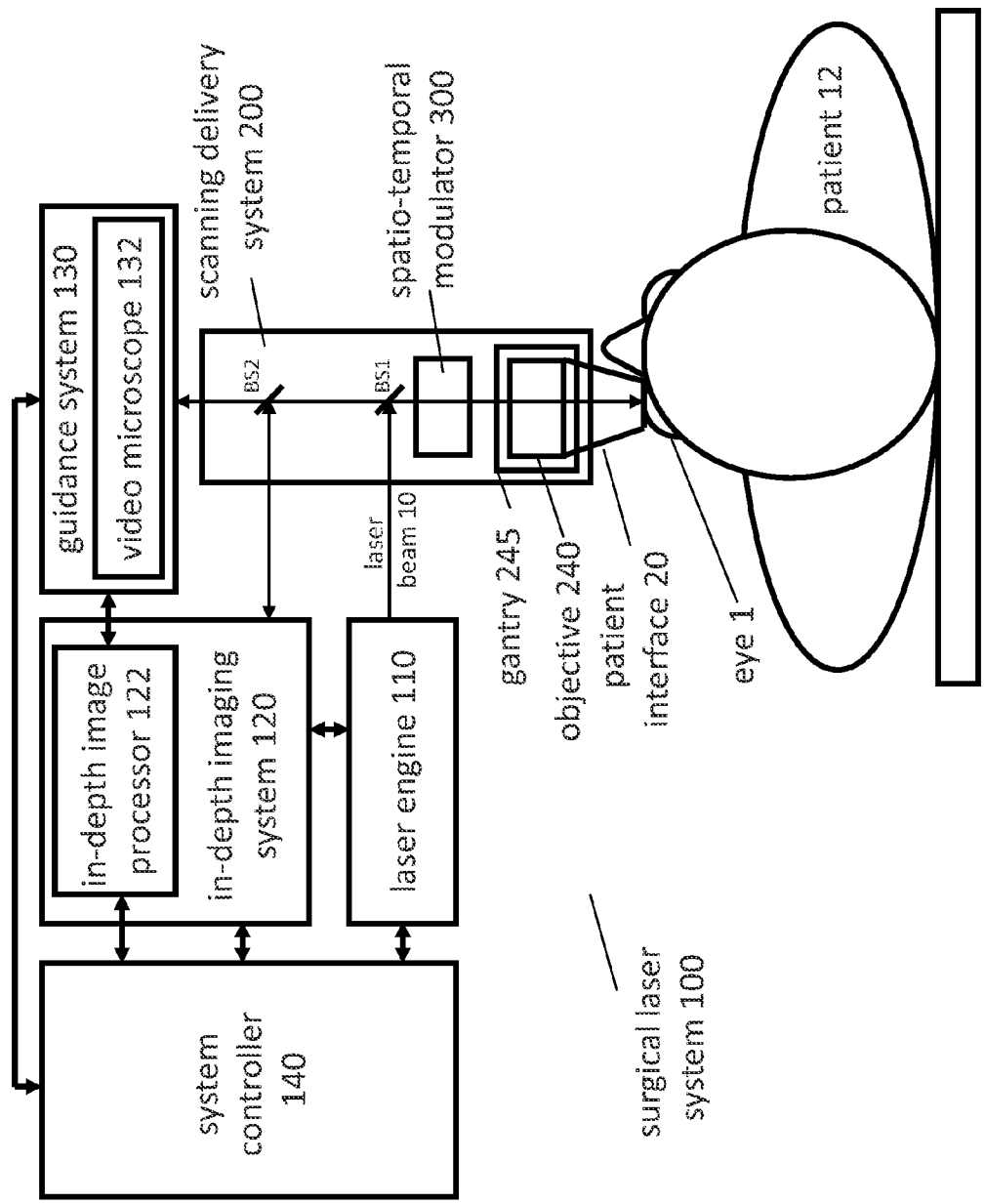
FIG. 5 illustrates an ophthalmic surgical laser system.

FIG. 5 illustrates an ophthalmic surgical laser system 100 that can include such a spatio-temporal beam modulator. The ophthalmic surgical laser system 100 can include a laser engine 110 that can generate a pulsed laser beam 10 to be directed and scanned into the eye 1. The laser system 100 can also include an in-depth imaging system 120 to generate images of the internal structure of the eye 1. The in-depth imaging system 120 can provide one or more in-depth images for the ophthalmic surgeon to increase the precision of the ophthalmic procedure. The in-depth imaging system 120 can be configured to generate a stereoscopic microscope image, a video-image, a Scheimpflug image, or an Optical Coherence Tomographic (OCT) image. The image can be analyzed by an image processor 122 of the in-depth imaging system 120.

The laser system 100 can also include a guidance system 130 to provide guidance information for the ophthalmic surgeon. In some embodiments, the guidance system 130 can include a video microscope 132 to display a video image of the eye 1. In others, the guidance system 130 can also include an in-depth display to display the in-depth image created by the in-depth imaging system 120. In yet others, the guidance system 130 can display both the video image and the in-depth image.

In some embodiments, the guidance system 130 can include a guidance display to guide the surgeon based on the result of the processing of the in-depth image of the imaging system 120 by the image processor 122. In others, the guidance system 130 can display the results of a processing of the video image of the video microscope 132 by a video image processor. For example, the guidance display of the guidance system 130 can include a target pattern or a crosshair pattern overlaid on the video image of the eye 1 to indicate a position of an optical center or axis of the laser system 100, thus allowing the surgeon to determine the position of the eye 1 relative to the optical axis. In other embodiments, the guidance system 130 can display a reference of the laser system 100 overlaid on the in-depth image, generated by the in-depth imaging system 120. These guidance displays can be used by the surgeon to dock the laser system 100 onto the eye with high precision and to plan and control the ophthalmic surgical procedure. The operations of the laser system 100 can be controlled and coordinated by a system controller 140.

The pulsed laser beam 10, generated by the laser engine 110 can be coupled into a scanning delivery system 200 at a beam splitter BS1. The laser engine 110 can be capable of generating the pulsed laser beam 10 with a pulse length in the femtosecond range (1-1,000 fs) or in the picosecond range (1-1,000 ps). The scanning delivery system 200 can redirect and deliver the pulsed laser beam 10 into the eye 1 of a patient 12 through an objective 240. The objective 240 can be movable by a gantry 245. The patient interface PI 20 can be attachable to the objective 240 to immobilize the targeted eye 1 relative to the objective 240 and to provide a controlled entry for the laser beam 10 into the eye 1.

Finally, the scanning delivery system 200 can include a spatio-temporal modulator 300, or space-time modulator 300, configured to perform a space- and time dependent modulation of the laser beam 10. The spatio-temporal modulator 300 can create a modulated component $\Phi_{mod}$ for the aberration function $\Phi$ in the Huygens-Fresnel integral that is additive to $\Phi_{aberration}$, the aberration caused by the wrinkled tissue and possibly the surgical laser system: $\Phi=\Phi_{aberration}+\Phi_{mod}$.

FIGS. 6-9 illustrate the principles of the operation of the spatio-temporal (ST) modulator 300, or S™ 300, while FIGS. 10-13 illustrate particular embodiments of the ST modulator 300.

Before proceeding with the detailed description, it is pointed out here that some existing systems attempt to reduce the effects of beam distortion by performing a diagnostics of the beam to determine the beam distortion by using e.g. a wavefront analyzer and then modifying the beam based on a feedback, generated from the determined beam distortion. These feedback systems increase the complexity of the system considerably, also increasing the number of elements that can (i) break down and require servicing, (ii) slow down the system's response time and operating speed, and that (iii) can increase the cost of the system.

In contrast, some embodiments of the spatio-temporal modulator 300 are operable without a beam diagnostic system or a wavefront analyzer, and do not need to include a feedback system either.

Instead of utilizing such diagnostic and feedback systems, in some embodiments the spatio-temporal modulator 300 can be configured to randomize the phase or the amplitude of the beam components of the laser beam on a modulation length scale and a modulation time scale. Such a randomization of the phases or amplitudes can be a comparably effective way to reduce the beam distortions caused by corneal wrinkling, while it does not add to the complexity of the laser system 100 and so it does not slow down its performance, require additional servicing, or increase the overall costs.

FIGS. 6A-C illustrate the operation of the ST modulator 300 in more detail. FIG. 6A illustrates the beam intensity with the STM 300 fixed at t, i.e. what the beam intensity would be, should the focus spot 32 of the laser beam 10 be scanned along a scan line while keeping the ST modulator 300 fixed in its configuration of time t. As it has been pointed out already in relation to FIG. 4B, corneal wrinkles 7 can reduce the beam intensity below the plasma threshold in extended no-cut or uncut regions, whose size can approach or exceed a millimeter. In the example of FIG. 6A, at the time t the focus spot 32 is scanned through a point x that belongs to such a no-cut region with the STM in its configuration at t where the corneal wrinkling caused such a destructive interference that the beam intensity is reduced below the plasma threshold over an extended no-cut region.

Should the ST modulator 300 remain fixed in its configuration of time t while the scanning of the focus spot continues, the focus spot will continue to scan through a region where the intensity of the laser beam is reduced by the corneal wrinkles below the plasma threshold over an extended no-cut region.

FIG. 6B illustrates that the STM 300 can change its configuration in a modulation time $\Delta t$ and shows what the beam intensity would be if the ST modulator 300 were fixed in its new configuration at the time t+Δt and the laser beam 10 scanned along the same scan line. Visibly, the ST modulator 300 can change the spatial modulation of the phase factors of the propagating electric fields in the modulation time Δt after the time t so that the no-cut regions of time t get either shifted by an amount comparable to their size (right no-cut region of FIG. 6A shifted in FIG. 6B), or get modified, reduced, or even eliminated altogether (left no-cut region of FIG. 6A having disappeared in FIG. 6B). In this same modulation time Δt, the scanning of the focus spot 32 may progress from x to x+Δx. As shown in FIG. 6B, the ST modulator 300 can be configured to spatio-temporally modify the beam so that its no-cut regions get shifted or modified to such a degree that at the time t+Δt the location x+Δx of the focus spot 32 falls outside the modified no-cut regions.

FIG. 6C summarizes the beam modification caused by the above-described operation of the ST modulator 300. To substantially reduce the spatial extent of the no-cut regions, the ST modulator 300 can be configured to rapidly change the spatial modulation of the laser beam 10. This space and time dependent, or "spatio-temporal" modulation of the laser beam 10 can cause the laser beam 10 to exhibit an effective beam intensity instead of the "fixed STM" beam intensities of FIGS. 6A-B as the focus spot 32 is scanned along the scan line.

In particular, even if the beam components exhibit a destructive interference at a time t at a position x, forcing the beam intensity below the plasma threshold and thus the focus spot 32 into a no-cut region, the STM 300 can cause the beam components to change their destructively interfering phase factors in a short modulation time Δt, thus shifting, modifying or eliminating the no-cut region at the location x+Δx by the time t+Δt the laser beam 10 is scanned through the location x+Δx along the scan line. Thus, the operation of the ST modulator 300 can make the scanned laser beam 10 to exhibit an effective beam intensity where the spatial extent of the "fixed STM" no-cut regions is reduced to much shorter effective no-cut regions. Therefore, the spatio-temporal modulation of the beam components by the ST modulator 300 can cause the laser beam 10 to maintain its beam intensity above the plasma threshold over a much higher fraction of the scan-pattern and to photodisrupt the target tissue successfully throughout the scan-pattern, interrupted only by much-shortened no-cut regions.

In some embodiments, the ST modulator 300 can be configured to reduce a length of a no-cut region, or equivalently an un-photo-disrupted scan-segment by a factor of more than 2 compared to the length of an un-photo-disrupted scan-segment made by the same surgical laser system 100 at the same location with the same corneal wrinkling but without the ST modulator 300.

FIGS. 7A-B illustrate the analogous reduction of the length or spatial extent of the no-cut regions when the laser system 100 that includes an ST modulator 300 follows a 2D scan-pattern 50. FIG. 7B illustrates that when the laser system follows the 2D scan-pattern 50, the operation of the ST modulator 300 can give rise to an effective beam intensity with no-cut regions whose size has been substantially reduced in both dimensions to the size of essentially a single bubble, as clear from a comparison of FIGS. 4A-B to FIGS. 7A-B.

Figure 8B:
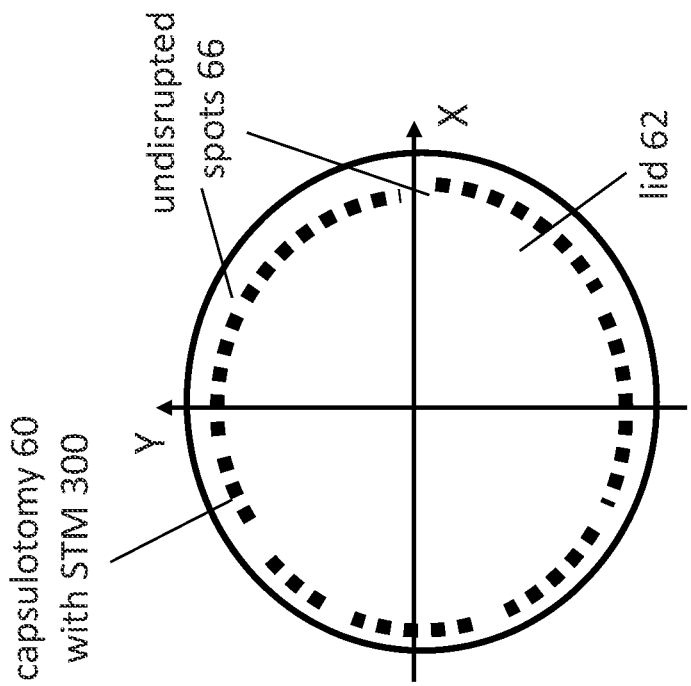
FIGS. 8A-B illustrate an effect of a spatio-temporal modulator on a photodisruption efficiency of a capsulotomy.
Figure 8A:
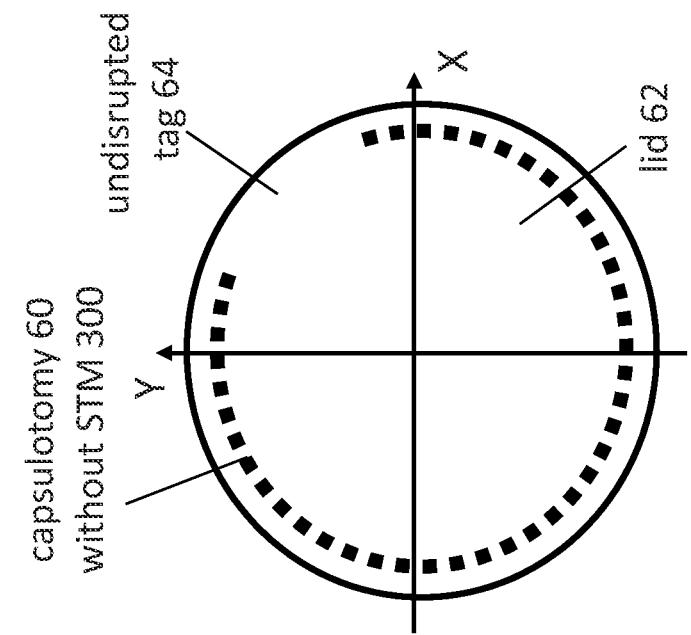

FIGS. 8A-B illustrate the operation of the ST modulator 300 in the context of a capsulotomy 60. FIG. 8A shows a typical circular capsulotomy 60, a circular or elliptical cut of the capsular bag, creating a lid 62. Having performed the capsulotomy 60, the surgeon removes the lid 62 to extract the lens 5 after the lens photodisruption.

However, in existing laser systems a corneal wrinkle 7 can reduce the intensity of the surgical laser beam 10 below the plasma threshold over a substantial no-cut region, forming an undisrupted tag 64. This undisrupted tag 64 requires the surgeon to manually complete the capsulotomy 60, possibly tearing the capsular bag or creating a jagged capsulotomy when removing the circular lid 62. Either of these possibilities can substantially reduce the precision of the cataract procedure itself and the subsequent insertion of an Intra Ocular Lens, or IOL, into the capsular bag.

FIG. 8B illustrates a capsulotomy 60, created by a laser system 100 that includes the spatio-temporal modulator 300. As described above, in the presence of the corneal wrinkles 7 the ST modulator 300 can modulate the beam components to substantially shorten the length of the no-cut regions 64 into undisrupted spots 66. During cataract surgeries with such laser systems, when the surgeon removes the lid 62, the tearing of the capsular bag at the short and localized undisrupted spots 66 will be minimal and well-controlled, thus maintaining the high precision attainable in the absence of corneal wrinkles.

Figure 9A:
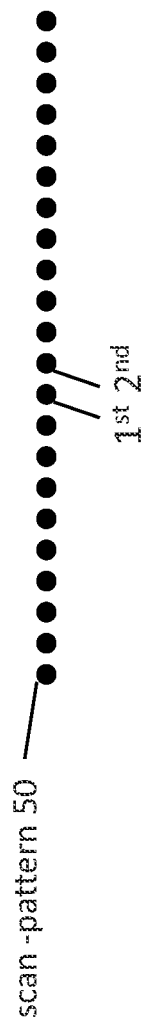
FIGS. 9A-C illustrate a location of a first and second spot along a scan line, along a returning scan-line and along a returning scan-segment.

FIG. 9A illustrates that in some surgical laser systems 100 the spatio-temporal modulator 300 can be configured to perform the space- and time dependent modulation of the laser beam components within a modulation time Δt less than 10 times T, a pulse repetition time of the laser pulses: T=1/f, f being the pulse repetition rate. In such embodiments, the modulation time Δt it takes for the ST modulator 300 to perform the spatio-temporal modulation, can be less than or comparable to the time T it takes the laser beam 10 to scan the focus spot 32 from a $1^{st}$ spot to a $2^{nd}$ spot, neighboring the $1^{st}$ spot or being very close to it.

In such embodiments the ST modulator 300 can shift or modify a potential no-cut region substantially while the focus spot 32 is scanned from the $1^{st}$ spot to the $2^{nd}$ nearby spot. Therefore, such an embodiment can reduce a potentially extended no-cut region to one or two un-photo-disrupted spots, drastically improving the precision of the surgical procedure, performed by the laser system 100.

Figure 9B:
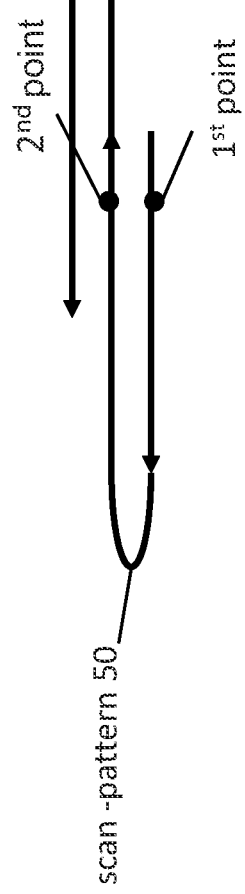

FIG. 9B illustrates that in some laser systems 100 the spatio-temporal modulator 300 can be configured to perform the space- and time dependent modulation of the beam components within a modulation time Δt that is smaller than or equal to a return time T(return) of the scan-pattern 50. Here, the scan-pattern 50 can include a set of closely spaced lines connected by switchbacks or hairpin turns, for example to perform a 2D cut or layer cut. The return time T(return) can be a time the scanning of the laser beam 10 takes between passing a $1^{st}$ point on a first line of the scan-pattern 50 and passing a $2^{nd}$ point on a second line of the scan-pattern 50 nearest to the $1^{st}$ point, as shown.

In such embodiments, even if the beam intensity at the $1^{st}$ point is below the plasma threshold, by the time the scanning of the laser beam reaches the $2^{nd}$ point, the ST modulator 300 changed the beam modulation to such a degree that the effective beam intensity is likely to be restored to its above-the-plasma-threshold level. Therefore, such embodiments can reduce the transverse spatial extent of potential no-cut regions to that of the transverse line separation. As FIG. 4B illustrated, without the STM 300 the corneal wrinkles 7 can form large no-cut regions with spatial extent in both the direction parallel and in the direction perpendicular or transverse to the direction of scanning. The embodiment of FIG. 9B can reduce this latter transverse extent of the no-cut regions substantially.

Figure 9C:
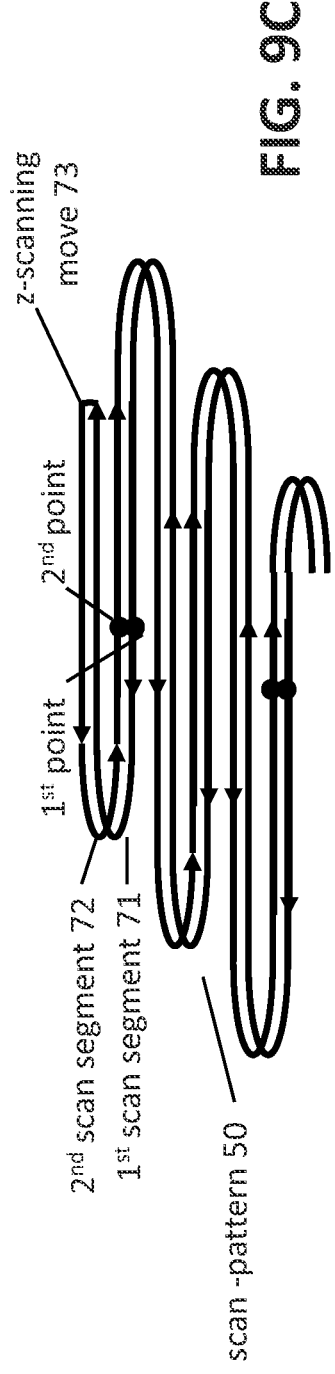

FIG. 9C illustrates that in some surgical laser systems 100 the ST modulator 300 can be configured to perform the space- and time dependent modulation of the beam components within a modulation time Δt less than a return time T(return) of the scan-pattern 50, wherein the scan-pattern 50 can include a set of closely spaced scan segments, and the return time T (return) can be a time the scanning of the laser beam 10 takes between passing a $1^{st}$ point on a $1^{st}$ scan-segment 71 of the scan-pattern 50 and a $2^{nd}$ point on a $2^{nd}$ scan-segment 72 of the scan-pattern 50, nearest to the first point. In the example of FIG. 9C, the first scan segment 71 can involve a first set of closely spaced lines in a transverse (x,y) plane, as in FIG. 9B. This can be followed by a z-scanning move 73 to a slightly anterior z coordinate along the optical axis of the laser system 100, connecting to the second scan segment 72 that includes a second set of closely spaced lines in the transverse (x,y) plane retracing the first scan segment 71 at the new slightly anterior z coordinate. Such cuts can be used to photodisrupt a volume of ophthalmic tissue, as is needed for the photodisruption of the lens 5 in the course of cataract surgery.

In sum, the list of the advantages of using the spatio-temporal modulator 300 in the laser system 100 includes the followings. (i) When corneal wrinkles cause the appearance of uncut regions, a normal response with a typical laser system is to increase the energy of the laser beam so that no uncut region is left behind. However, such an increase of the beam energy can cause collateral damage in the form of overheating and shockwaves in the ophthalmic tissue. In laser systems that include the STM 300, even in the presence of corneal wrinkling the surgical goals such as a clean capsulotomy can still be achieved without increasing the beam energy. This is so because, while the corneal wrinkles can still distort the laser beam to leave uncut regions, the inclusion of the STM 300 substantially reduces the spatial extent of these uncut regions, and these short uncut regions can be comfortably cut manually by the surgeon later without causing jagged edges or tearing. Thus, laser systems with the STM 300 eliminate the need to increase the pulse energy of the laser beam in the presence of corneal wrinkling. This aspect also allows laser systems with the STM 300 to reduce the overall exposure time of the targeted ophthalmic tissues.

(ii) Referring back to FIGS. 3A-C, the jagged, double cut and sometimes discontinuous cut lines that can appear during a capsulotomy in the presence of corneal wrinkling can be also eliminated by the inclusion of the ST modulator 300 in the laser system 100.

(iii) Finally, incorporating the ST modulator 300 into the laser system 100 can also make re-tracing a surgical cut or portions of it much more effective. In an example, after performing a surgical beam scan the surgeon may observe that the scan still left an undesirably long uncut section, and may decide to rescan the uncut section. In a laser system without the STM 300, the rescanning does not promise an improvement, as the corneal wrinkles will once again cause a destructive interference between the beam components, thus preventing the cut even during the rescan. In contrast, in a laser system that includes the STM 300, by the time the uncut section is rescanned, the STM 300 changes the beam modulation and thus substantially reduces or eliminates the destructive interference for the rescan of the uncut section. In other words, since the phases of the beam components are modulated differently during the first scan and the rescan, the interferences, which were destructive during the first scan and gave rise to uncut portions, change substantially during the rescan, so that the uncut regions of the first scan get filled in by the subsequent rescan. Rescanning can include scanning along the same scanning track or scanning in the vicinity of the previous cut, preferably within the plasma-tissue interaction length. When cutting with a femtosecond laser, this plasma-tissue interaction length is typically the diameter of the laser-induced cavitation bubbles in the tissue, often in the 1-20 micrometer range. In an example, a capsulotomy can include performing repeated circular cuts at a sequence of z depths moving in a posterior-to-anterior direction, the circular cuts being separated by a few micrometers and thus creating a macroscopic cut shaped like a cylinder. Re-scanning can be performed as an intervention by the surgeon, as an intervention by the control system, or be pre-programmed into the control system software without feedback.

After having described the operation and impact of the spatio-temporal modulator 300, its various embodiments are described next.

Figure 10A:
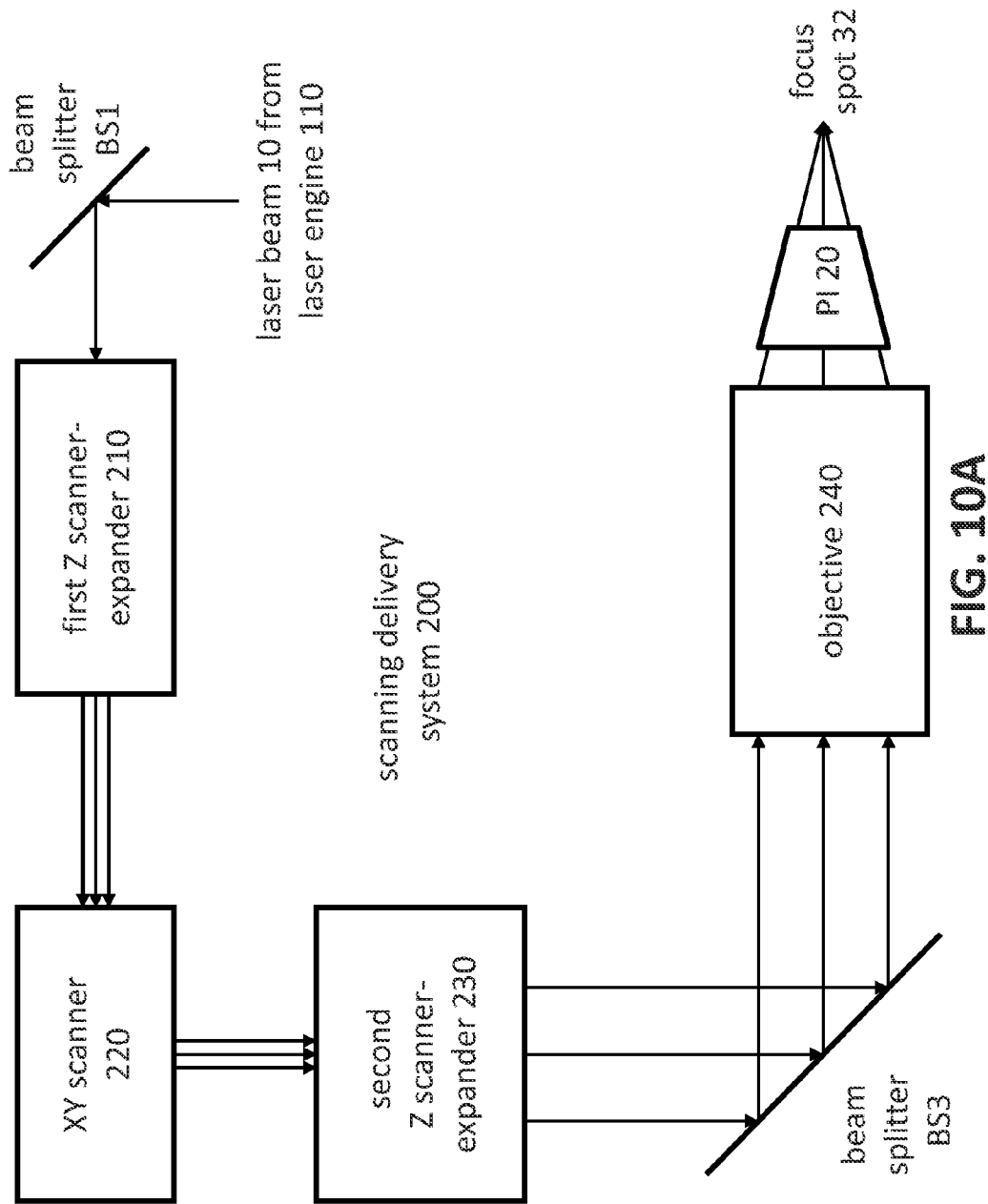
FIGS. 10A-B illustrate a scanning delivery system and possible locations of a spatio-temporal modulator in different embodiments.

FIG. 10A illustrates an embodiment of the scanning delivery system 200 in more detail. The laser beam 10 can enter the scanning delivery system 200 via the beam splitter BS1 and can proceed to a first Z scanner-expander 210 that can expand a radius of the laser beam 10 and can also play a part in scanning the z longitudinal or depth coordinate of the focus spot 32 in the target region or tissue. From the first Z scanner-expander 210, the expanded laser beam 10 can propagate to an XY scanner 220 that is configured to scan the focus spot 32 in the transverse (x,y) plane in the target region or tissue.

From the XY scanner 220, the laser beam 10 can propagate to a second Z scanner-expander 230 whose functions can be similar to that of the first Z scanner-expander 210. Various embodiments of the scanning delivery system 200 may include only one of the two Z scanner-expanders 210 and 230. The functions of the Z scanner-expanders 210 and 230 can include scanning the z longitudinal or depth coordinate of the focus spot 32 in the target region or tissue. The scanning delivery system 200 can also include the objective 240, to which the laser beam may be redirected by a beam splitter BS3. The objective 240 can focus the expanded laser beam into a high numerical aperture (high NA) focused beam and deliver it to the target region through the patient interface (PI) 20. Generating a high NA beam can ensure that the laser beam 10 causes photodisruption only at the intended z depth or longitudinal coordinate, thus avoiding collateral damage posterior or anterior relative to the target region. In some embodiments, NA can be in the 0.15-0.45 range. In some others, it can be in the 0.25-0.35 range.

Figure 10B:
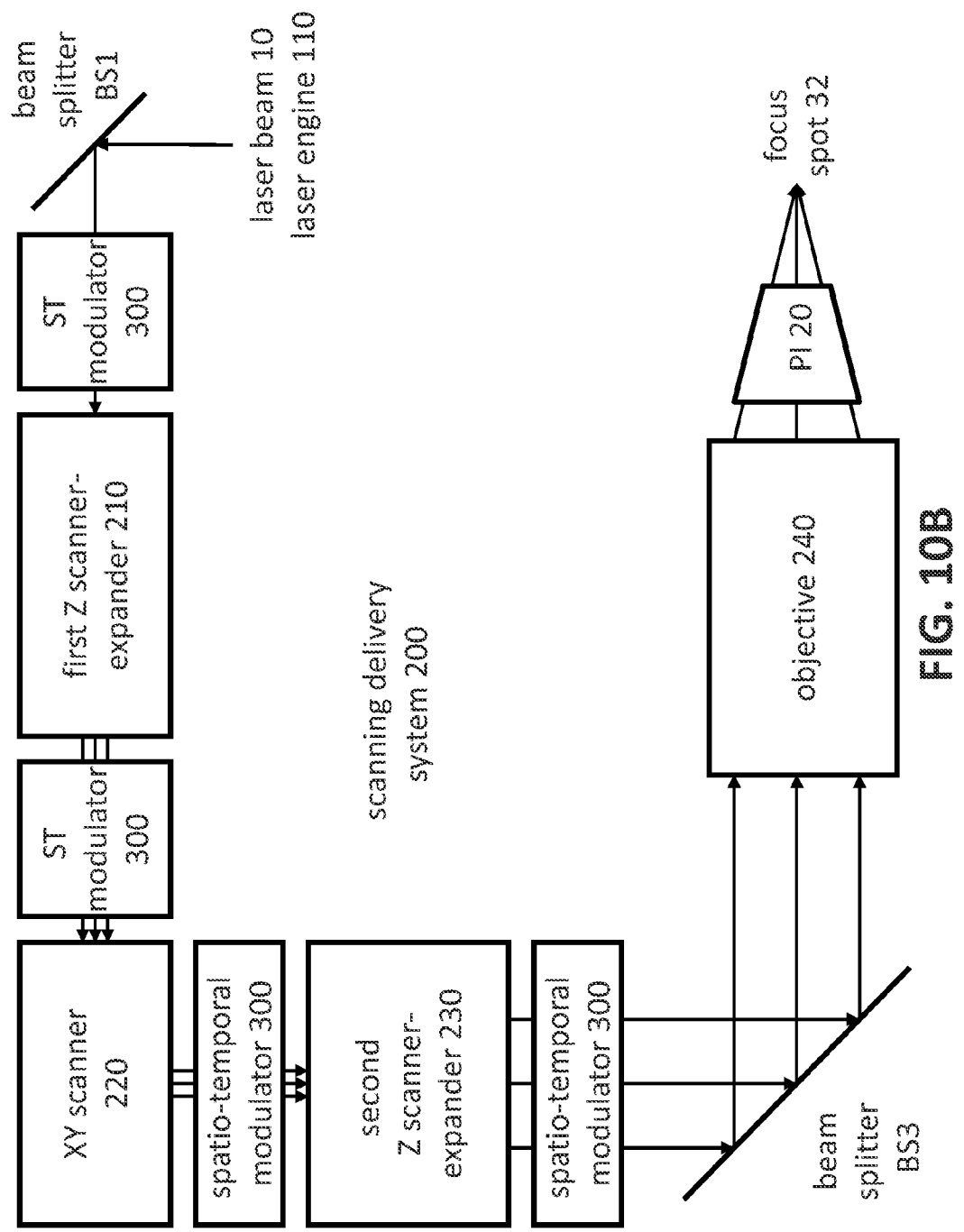

FIG. 10B illustrates that in various embodiments of the scanning delivery system 200 the spatio-temporal modulator 300 can be disposed at different locations along an optical path of the laser beam 10, including: before the first Z scanner-expander 210, between the first Z scanner-expander 210 and the XY scanner 220, between the XY scanner 220 and the second Z scanner-expander 230, and between the second Z scanner 230 and the objective 240. The ST modulator 300 can be disposed at any one of these locations.

In various embodiments, the spatio-temporal modulator 300 can be a transmissive modulator, an absorptive modulator or a reflective modulator, inserted into the beam path accordingly.

Figure 11:
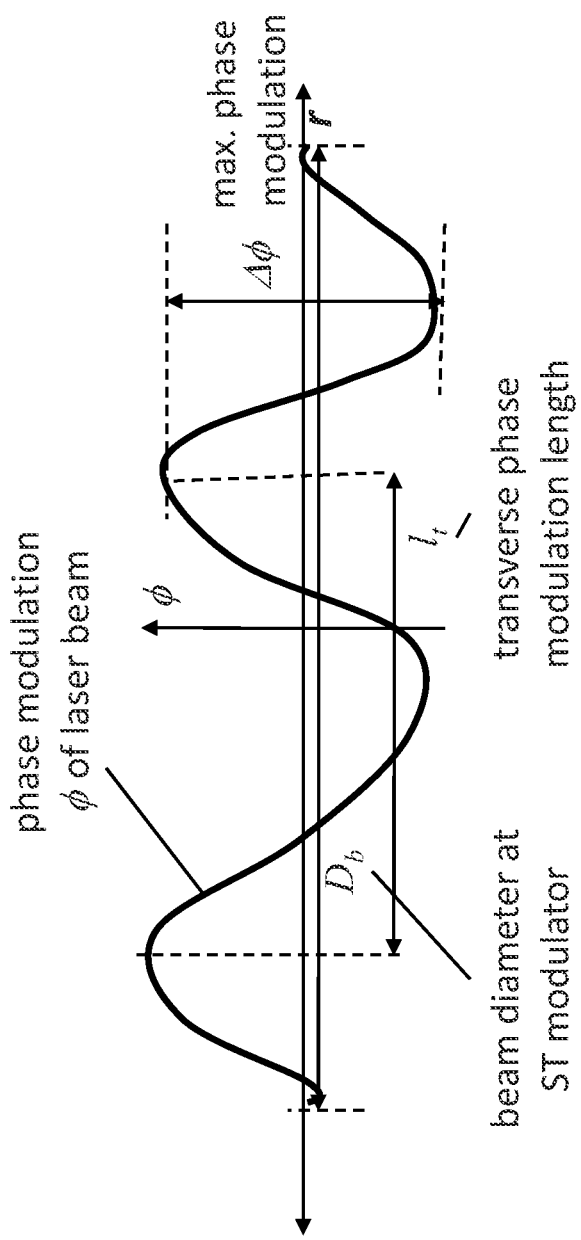
FIG. 11 illustrates a phase modulation of the laser beam.

FIG. 11 illustrates that the spatio-temporal modulator 300 can be configured to perform the space- and time dependent modulation of the laser beam by modulating the phase or aberration Φ of the beam components. FIG. 11 illustrates that the phase Φ can be modulated across the beam diameter $D_b$ at the spatio-temporal modulator 300 on a transverse phase modulation length $l_t$, where the transverse modulation length $l_t$ can be less than the beam diameter $D_b$ at the spatio-temporal modulator 300. When the modulation length $l_t$ is less than the beam diameter $D_b$, the ST modulator 300 can modulate the phases of the beam components differently, reducing or eliminating the destructive interferences at the focal plane in the target region, caused by distortion centers, such as the corneal wrinkles 7. In some embodiments of the laser system 100, $D_b$ can be in the range 5-30 mm, in others, in the range of 10-20 mm. $l_r$ can be in the range of 0.05-2 mm, in some cases in the 0.2-1 mm range. Finally, in some embodiments, $\Delta\Phi$, the maximum of the phase modulation can be at least $\pi/4$.

FIGS. 12A-D illustrate various embodiments of the spatio-temporal modulator 300. These embodiments can be used effectively to modulate the phase factors of the beam components of the laser beam 10. FIG. 12A illustrates that some ST modulators 300 can include a rotatable wheel 310 with a surface 312 that has a height variation with an amplitude between $0.1\lambda$ and $10\lambda$, wherein $\lambda$ is a wavelength of the laser beam 10. In other embodiments, the rotatable wheel 310 can have an optical path length variation in the same $0.1\lambda$ to $10\lambda$ range. This height variation can provide the spatial phase modulation of the beam components. The wheel 310 can spin around an axis 314, making the spatial phase modulation also time dependent, or temporal. The speed of rotation of the wheel 310 can determine whether the modulation time $\Delta t$ is less than an inverse pulse repetition rate, or a scan line return time or a scan segment return time T(return). As mentioned above, this and the later described embodiments can be all implemented in a transmissive, absorptive or reflective mode.

FIG. 12B illustrates an embodiment of the ST modulator 300 that includes an LCD array 320 that includes a large number of LCD pixels 322. The LCD pixels 322 can be controlled individually or is small groups to modulate the phase of the laser beam 10 in spatially varying manner. Further, the state of the LCD pixels 322 can be electronically varied with time, making the spatially varying phase modulation time dependent as well. In related embodiments, the ST modulator 300 can include an array of other types of electronically controllable electro-optical phase modulators.

FIG. 12C illustrates that some embodiments of the ST modulator 300 can include an acousto-optical phase modulator 330. In some cases the acousto-optical phase modulator can include a set of acoustic piezo transducers 332, positioned to be able to deform a deformable reflector 334. The transducers 332 deforming the deformable reflector 334 in various patterns can modulate the phase of the laser beam 10 in a spatially dependent manner. The transducers 332 can be controlled electronically to make the spatial phase modulation also time dependent.

Finally, FIG. 12D illustrates that some embodiments of the ST modulator 300 can include a deformable mirror or reflector 340, deformable by an array of mechanical actuators 342, disposed on a substrate 344. The array of the mechanical actuators 342 can make the phase modulation spatially dependent, and the time-dependent control of the actuators 342 can make the spatial modulation also temporal modulation.

While FIGS. 12A-D described reflective embodiments of the ST modulators 300, analogous embodiments that are transmissive or absorbing also exist. For example, in FIG. 12A the rotating wheel 310 with the rough surface 312 can be made not from a reflective material but from a transmissive or absorbing material to modulate the phase of the laser beam 10 as it transits the wheel 310.

It is noted here that optical elements with a linearly varying surface may not be useful as STM 300s, as they can redirect the laser beam 10 without randomizing their phases with a spatio-temporal modulation. Therefore, embodiments of the ST modulator 300 may include optical elements that are configured to perform a time-dependent phase modulation that is a non-linear function of a coordinate across a beam aperture of the laser beam 10.

FIGS. 13A-B illustrate embodiments of the ST modulator 300 that are configured to perform a space- and time dependent amplitude modulation of the laser beam 10.

FIG. 13A illustrates an ST modulator 300 that includes a rotatable wheel 350 with a transmission coefficient that varies with a transmission modulation length shorter than a beam diameter at the ST modulator 300. For example, in some embodiments a concentration of a dopant or an impurity can be varied in the rotatable wheel 350, made of glass. In other embodiments, variable transmission pixels or elements 352 can be installed on the rotatable wheel 350. The rotatable wheel 350 can be rotated around an axis 354, making the amplitude modulation time dependent. It is mentioned here that in addition to absorption, the refractive index of the wheel 350 can also be changed with suitable dopants. Finally, an embodiment of the phase ST modulator 300 can also be constructed in a similar fashion.

FIG. 13B illustrates an embodiment of the ST modulator 300 that includes a pixel array 360, made of a large number of variable transparency pixels 362. Similarly to FIG. 12B, the independent control of the transparency of the pixels 362 can introduce a spatially dependent amplitude modulation, and the time dependent varying of the transparency of the pixels 362 by electronic control systems can make the spatial modulation temporal as well.

While the embodiments of FIGS. 12A-D were described in the context of phase modulation, whereas the embodiments of FIGS. 13A-B were described in the context of amplitude modulation, each embodiment can be used for both phase and amplitude modulation. For example, the LCD pixels 322 of FIG. 12B can be used in transmissive mode, acting as the variable pixels 362 of FIG. 13B.

Figure 14:
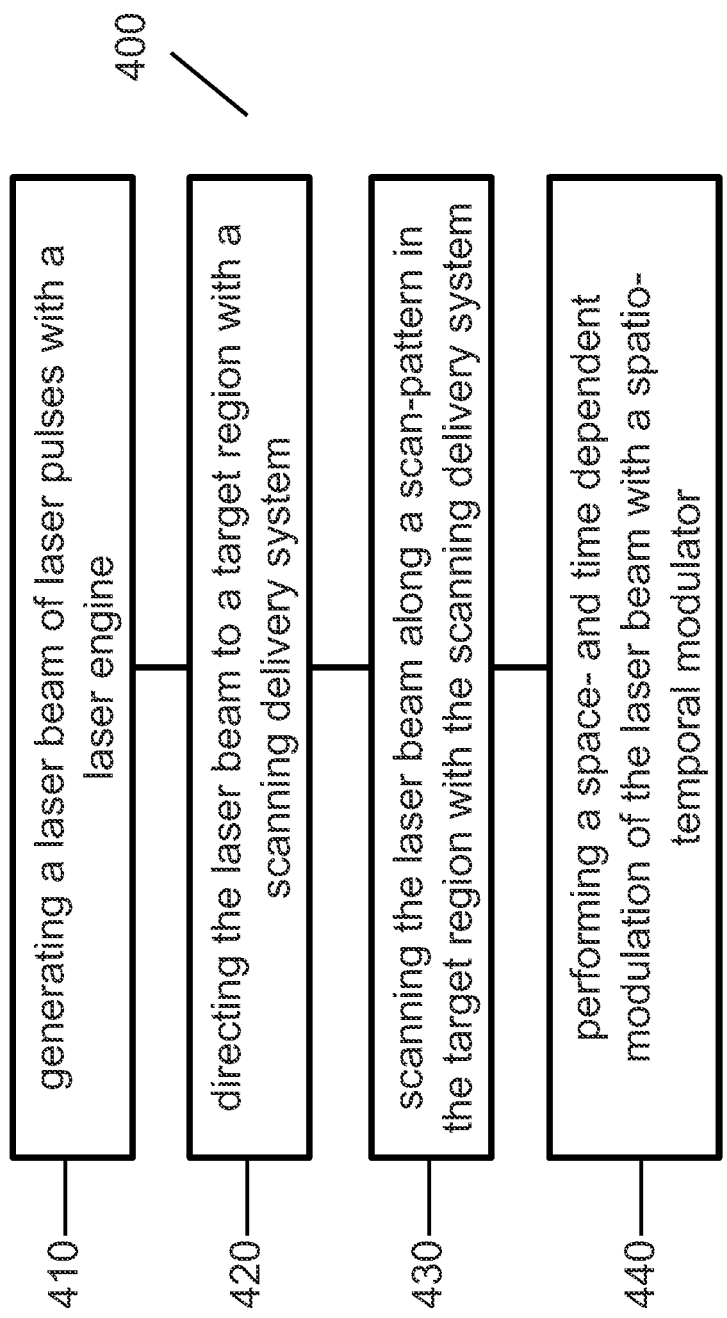
FIG. 14 illustrates a method of homogenizing a laser beam with a spatio-temporal modulator.

FIG. 14 illustrates a method 400 of homogenizing a laser beam. The method 400 can include a generating 410 of a laser beam of laser pulses with a laser engine; a directing 420 of the laser beam to a target region with a scanning delivery system; a scanning 430 of the laser beam along a scan-pattern in the target region with the scanning delivery system; and a performing 440 of a space- and time dependent modulation of the laser beam with a spatio-temporal modulator.

During the performing 440 the space- and time dependent modulation can be performed within a modulation time $\Delta t$ less than 10 times a pulse repetition time of the laser pulses.

During the performing 440 the space- and time dependent modulation can be performed within a return time of the scan-pattern, wherein the scan-pattern includes a set of closely spaced lines, and the return time is a time the scanning of the laser beam takes between passing a first point on a first line of the scan-pattern and a second point on a second line of the scan-pattern nearest to the first point.

During the performing 440, the space- and time dependent modulation can be performed within a return time of the scan-pattern, wherein the scan-pattern includes a set of closely spaced scan segments, and the return time is a time the scan of the laser beam takes between passing a first point on a first scan segment and a second point on a second scan segment nearest to the first point.

The performing 440 can include performing a space- and time dependent phase modulation of the laser beam. In other embodiments, the performing 440 can include performing a space- and time dependent amplitude modulation of the laser beam.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

What is claimed is:

1. A surgical laser system, comprising:
a laser engine, configured to generate a laser beam of laser pulses;
a scanning delivery system, configured
   to direct the laser beam to a target region, and
   to scan the laser beam along a scan-pattern in the target region; and
a spatio-temporal modulator, configured to perform a space- and time dependent modulation of the laser beam by randomizing at least one of a phase and an amplitude of beam components of the laser beam.

2. The surgical laser system of claim 1, wherein:
the spatio-temporal modulator is operable without at least one of a beam diagnostic system, a wavefront analyzer and a feedback system.

3. The surgical laser system of claim 1, wherein:
the spatio-temporal modulator is configured to randomize at least one of a phase and an amplitude of beam components of the laser beam on a modulation length and a modulation time.

4. The surgical laser system of claim 1, wherein:
the spatio-temporal modulator is configured to reduce a length of an un-photo-disrupted scan-segment left behind when the laser beam is scanned through a distorted region of the target region by a factor of more than 2 compared to the length of an un-photo-disrupted scan-segment left behind when the same surgical laser system is scanned through the same target region but without the spatio-temporal modulator.

5. The surgical laser system of claim 1, wherein:
the spatio-temporal modulator is configured to perform the space- and time dependent modulation having a spatial variation with a transverse modulation length less than a beam diameter at the spatio-temporal modulator.

6. The surgical laser system of claim 1, wherein:
the spatio-temporal modulator is configured to perform the space- and time dependent modulation within a modulation time less than 10 times a pulse repetition time of the laser pulses.

7. The surgical laser system of claim 1, wherein:
the spatio-temporal modulator is configured to perform the space- and time dependent modulation within a modulation time less than a return time of the scan-pattern, wherein
   the scan-pattern includes a set of closely spaced lines, and
   the return time is a time the scan of the laser beam takes between passing a first point on a first line of the scan-pattern and a second point on a second line of the scan-pattern nearest to the first point.

8. The surgical laser system of claim 1, wherein:
the spatio-temporal modulator is configured to perform the space- and time dependent modulation within a modulation time less than a return time of the scan-pattern, wherein
   the scan-pattern includes a set of closely spaced scan segments, and
   the return time is a time the scan of the laser beam takes between passing a first point on a first scan-segment of the scan-pattern and a second point on a second scan-segment of the scan-pattern nearest to the first point.

9. The surgical laser system of claim 1, wherein:
the scanning delivery system is configured to rescan the laser beam with a second modulation along a portion of the scan-pattern that has been already scanned with a first modulation, wherein
the first modulation is different from the second modulation.

10. The surgical laser system of claim 1, wherein:
the scanning delivery system comprises
   at least one of a first Z scanner-expander and a second Z scanner-expander,
   an XY scanner, and
   an objective; and
the spatio-temporal modulator is positioned at one of a location along an optical path of the laser beam
   before the first Z scanner-expander,
   between the first Z scanner-expander and the XY scanner,
   between the XY scanner and the second Z scanner-expander, and
   between the second Z scanner and the objective.

11. The surgical laser system of claim 1, wherein:
the spatio-temporal modulator is at least one of a transmissive modulator, an absorptive modulator and a reflective modulator.

12. The surgical laser system of claim 1, wherein:
the spatio-temporal modulator is configured to perform a space- and time dependent phase modulation of the laser beam.

13. The surgical laser system of claim 12, wherein:
the spatio-temporal modulator is configured to introduce a spatially dependent phase modulation of the laser beam with a maximum phase modulation of at least $\pi/4$.

14. The surgical laser system of claim 12, the spatio-temporal modulator comprising:
a rotatable wheel configured to cause an optical path length variation with an amplitude between $0.1\lambda$ and $10\lambda$, wherein $\lambda$ is a wavelength of the laser beam.

15. The surgical laser system of claim 12, the spatio-temporal modulator comprising:
an array of electronically controllable electro-optical phase modulators.

16. The surgical laser system of claim 12, the spatio-temporal modulator comprising:
an acousto-optical phase modulator.

17. The surgical laser system of claim 12, the spatio-temporal modulator comprising:
a deformable mirror, deformable by an array of mechanical actuators.

18. The surgical laser system of claim 1, wherein:
the spatio-temporal modulator is configured to perform a time-dependent phase modulation that is a non-linear function of a coordinate across a beam aperture.

19. The surgical laser system of claim 1, wherein:
the spatio-temporal modulator is configured to perform a space- and time dependent amplitude modulation of the laser beam.

20. The surgical laser system of claim 19, the spatio-temporal modulator comprising:
- a rotatable wheel with a transmission coefficient varying at a transmission length shorter than a beam diameter at the spatio-temporal modulator.

21. The surgical laser system of claim 19, the spatio-temporal modulator comprising:
- an array of variable transparency pixels.

22. A method of homogenizing a laser beam, the method comprising:
- generating a laser beam of laser pulses with a laser engine;
- directing the laser beam to a target region with a scanning delivery system;
- scanning the laser beam along a scan-pattern in the target region with the scanning delivery system; and
- performing a space- and time dependent modulation of the laser beam with a spatio-temporal modulator by randomizing at least one of a phase and an amplitude of beam components of the laser beam.

23. The method of claim 22, wherein:
- the space- and time dependent modulation is performed within a modulation time less than 10 times a pulse repetition time of the laser pulses.

24. The method of claim 22, the performing a space- and time dependent modulation comprising:
- performing a space- and time dependent phase modulation of the laser beam.

\* \* \* \* \*